United States Patent [19]
Nakayama et al.

[11] Patent Number: 5,902,108
[45] Date of Patent: May 11, 1999

[54] AIR TURBINE HANDPIECE

[75] Inventors: Shozo Nakayama; Haruo Ogawa; Makoto Numakawa; Hirofumi Jikuhara; Hajime Yokota, all of Kyoto, Japan

[73] Assignee: J. Morita Manufacturing Corporation, Kyoto, Japan

[21] Appl. No.: 09/028,391

[22] Filed: Feb. 24, 1998

[30] Foreign Application Priority Data

Feb. 25, 1997 [JP] Japan ................................ 9-041183

[51] Int. Cl.⁶ ................................................ A61C 1/05
[52] U.S. Cl. .......................................... 433/132; 415/904
[58] Field of Search ................................. 433/132, 106; 415/904

[56] References Cited

U.S. PATENT DOCUMENTS

| | | |
|---|---|---|
| 3,386,702 | 6/1968 | Krzyszczuk . |
| 3,469,318 | 9/1969 | Saffir ........................................ 433/132 |
| 4,020,556 | 5/1977 | Sotman . |
| 4,146,964 | 4/1979 | Lares et al. ............................. 433/132 |
| 4,326,846 | 4/1982 | Sugai et al. ............................. 433/132 |
| 5,312,252 | 5/1994 | Abbott .................................... 433/132 |
| 5,374,189 | 12/1994 | Mendoza ................................. 433/132 |
| 5,562,446 | 10/1996 | Matsui et al. ........................... 433/132 |
| 5,667,383 | 9/1997 | Mendoza et al. ....................... 433/132 |

*Primary Examiner*—Nicholas D. Lucchesi
*Attorney, Agent, or Firm*—Koda & Androlia

[57] ABSTRACT

An air turbine handpiece comprises a grip portion and a head portion disposed at a tip of the grip portion. In the handpiece, a rotor is disposed in a chamber in the head portion, and a cutting tool is detachably attached to a rotation shaft which is rotated integrally with the rotor. A nozzle opening for injecting air toward a turbine blade portion and an exhaust opening for exhausting the injected air to the outside are opened to the chamber of the head portion. An arc width of the nozzle opening in a circumferential direction is two or more times a height in a direction of a rotation axis of the rotor. The nozzle opening is formed so as to extend in a width direction.

33 Claims, 12 Drawing Sheets

FIG. 4
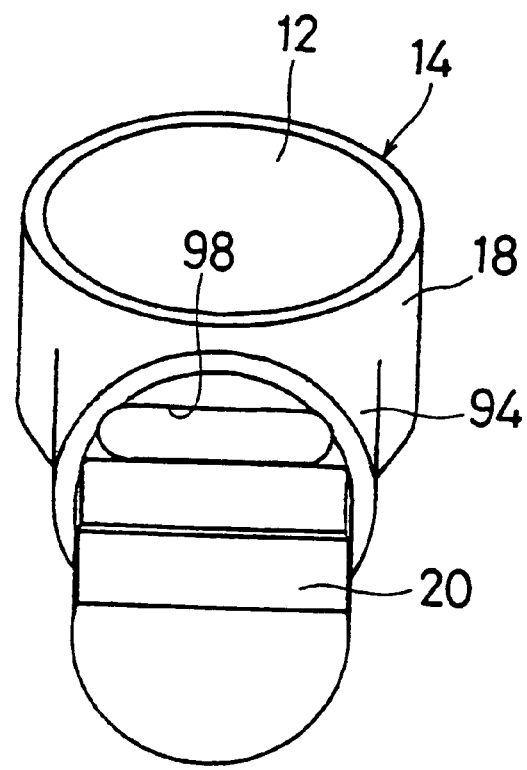
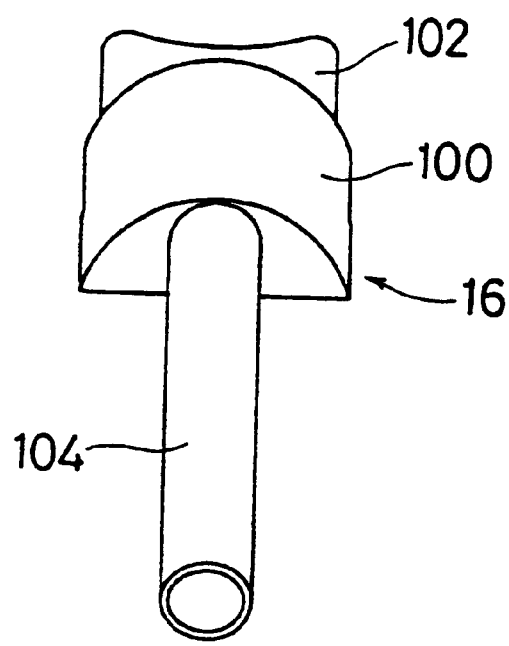

AIR TURBINE HANDPIECE

BACKGROUND OF THE INVENTION

1. Field of the Invention

The present invention relates to an air turbine handpiece which can be usefully applied to medical treatment or the like.

2. Description of the Related Art

A medical handpiece, preferably a dental handpiece is disclosed in, for example, U.S. Pat. No. 4,020,556. The known handpiece comprises a grip portion and a head portion which is disposed at an tip of the grip portion. A chamber is formed in the head portion. A rotor having a turbine blade portion is rotatably disposed in the chamber. A rotation shaft is attached to the rotor. A cutting tool is detachably attached to the rotation shaft. A supply tube for supplying compressed air to the turbine blade portion is incorporated in the grip portion. Two nozzle tubes are connected to a tip of the supply tube, and tip openings of the two nozzle tubes are opened to the chamber. In the chamber, exhaust openings are formed above and below the tip openings of the two nozzle tubes, and exhaust flow paths extends from the exhaust openings through the grip portion along a direction of its length. The turbine blade portion has a plurality of turbine blades which are arranged in a circumferential direction at intervals. Operating surfaces (the surface to which air is injected from the nozzle tubes) of the turbine blades arcuately extend in the vertical direction. In the handpiece, the compressed air is injected through the supply tube and the nozzle tubes toward the turbine blades of the turbine blade portion, and the turbine blade portion, the rotation shaft, and the cutting tool are rotated in a specified direction by the injected compressed air. The air which is injected to the turbine blades flows in upward and downward directions along the operating surfaces of the blades and is then exhausted to an outside through the exhaust openings which are formed above and below the nozzle tubes.

Another handpiece is disclosed, for example, in U.S. Pat. No. 3,386,702. The handpiece has a rotor which is rotatably disposed in a chamber. A rotation shaft is fixed to the rotor, and a cutting tool is attached to the rotation shaft. The rotor has first and second turbine blade portions which are separately arranged in an axial direction of the rotor. Each of the first and second turbine blade portions has first and second portions which are arranged in the circumferential direction at intervals. Plural stationary guide vanes for guiding air from the first turbine blade portion to the second turbine blade portion are arranged between the first and second turbine blade portions. A nozzle opening is disposed above the first turbine blade portion of the rotor, and an exhaust opening is disposed below the second turbine blade portion. Air injected from the nozzle opening acts on the turbine blade of the first turbine blade portion and flows along the turbine blade portions. The air is then guided by the stationary guide vanes from the first turbine blade portion to the second turbine blade portion to act on the second turbine blade portions of the second turbine blade portion and thereafter exhausted to the outside through the exhaust opening. In this way, air from the nozzle opening acts on the turbine blade portions of the first and second turbine blade portions. Therefore, the rotor is rotated at relatively high rotation torque.

However, these handpieces have the following problems which are to be solved.

First, when a handpiece is used, for example, in dental treatment, a rotor, i.e., a cutting tool is rotated at a very high velocity of about 400,000 rpm. In order to rotate the rotor at such a high velocity, it is important to efficiently inject compressed air from a nozzle tube, i.e., a nozzle opening toward a turbine blade portion. In the above-described prior art handpieces, however, the nozzle tube has a tip opening which is approximately circular, and hence the rotor cannot be sufficiently efficiently rotated. More specifically, when a nozzle tube has a small tip opening, compressed air acts concentrically on turbine blades of a turbine blade portion but it is difficult to rotate a rotor at high torque because an injection quantity of the compressed air is small. By contrast, when a nozzle tube has a large tip opening, the compressed air is injected to a relatively wide area of each turbine blade of the turbine blade portion and the injection quantity of the compressed air is increased. However, also a quantity of waste air which does not substantially contribute to generating the rotation torque is also increased. The waste air may become as a rotation resistance to the rotor.

Second, the operating surface of each turbine blade of the turbine blade portion extends simply in an arcuate form. Therefore, air injected to the operating surfaces of turbine blades flows upward and downward (or downward) along the operating surfaces of the turbine blades but the air flow is not smoothly conducted. Furthermore, a part of the air which flows upward and downward (or downward) from the operating surfaces of the turbine blades functions as a resistance to the rotation of the turbine blades. As a result, the kinetic energy of the air cannot be converted into the rotation energy of the rotor.

Third, particularly in the handpiece disclosed in U.S. Pat. No. 3,386,702, the rotor comprises the first and second turbine blade portions and the stationary guide vanes are disposed between the first and second turbine blade portions, and hence the head portion with the rotor incorporated in it is larger. The nozzle opening is disposed above the first turbine blade portion and driving air is injected from an upper side to an obliquely lower side. This configuration also causes the head portion to be larger. This configuration has a further disadvantage that the energy of the air cannot be sufficiently efficiently converted into the rotation energy of the rotor. When the head portion is large, it is difficult to perform a cutting operation of molars or dental treatment for children.

SUMMARY OF THE INVENTION

An object of the invention is to provide an air turbine handpiece in which a rotor can be efficiently rotated at high torque, in connection with a nozzle opening for injecting air to a turbine blade portion.

Another object of the invention is to provide an air turbine handpiece in which air injected to turbine blades of a turbine blade portion flows smoothly so that a rotor can be efficiently rotated.

A further object of the invention is to provide an air turbine handpiece which comprises first and second turbine blade portions, and in which a height of a head portion can be reduced and a kinetic energy of air can be efficiently converted into a rotation energy of a rotor.

In a first aspect of the invention, an air turbine handpiece comprises a grip portion, a head portion disposed at a tip of the grip portion, and a rotor having a turbine blade portion, disposed in a chamber formed in the head portion, the rotor being rotatably supported via bearing means, integrally with a rotation shaft, a tool being detachably attached to the rotation shaft, wherein a nozzle opening for injecting air toward the turbine blade portion of the rotor, and an exhaust opening for exhausting the injected air to an outside are opened to the chamber of the head portion, and an arc width W of the nozzle opening in a circumferential direction is set to two or more times a height H of the rotor in a rotation axial direction.

According to the first aspect of the invention, the arc width W in the circumferential direction of the nozzle opening for injecting air to the turbine blade portion is set to two or more times the height H in the rotation axial direction of the rotor, and the nozzle opening extends in the circumferential direction. Therefore, the air injected from the nozzle opening can concentrically act on the center portions in an axial direction of turbine blades of the turbine blade portion. Since the nozzle opening has a large area, a supply quantity can be increased. Consequently, the rotor can be efficiently rotated at high torque.

In a second aspect of the invention, the arc width W of the nozzle opening in the circumferential direction is three to twenty times the height H in the rotation axial direction of the rotor ($3H \leq W \leq 20H$).

According to the second aspect of the invention, since the arc width W of the nozzle opening in the circumferential direction is three to twenty times the height H in the rotation axial direction of the rotor, it is possible to ensure a sufficiently large opening area of the nozzle opening even when the height H in the rotation axial direction is reduced. Consequently, the rotor can be efficiently rotated at high torque.

In a third aspect of the invention, the arc width W of the nozzle opening in the circumferential direction is seven to fifteen times the height H in the rotation axial direction of the rotor ($7H \leq W \leq 15H$).

According to the third aspect of the invention, since the arc width W of the nozzle opening in the circumferential direction is seven to fifteen times the height H in the rotation axial direction of the rotor, a ratio of the height H of the nozzle opening to the arc width W has an appropriate value. Consequently, the rotor can be more efficiently rotated at high torque.

In a fourth aspect of the invention, a plurality of turbine blades are arranged in the turbine blade portion in the circumferential direction at substantially regular intervals, and the arc width W in the circumferential direction of the nozzle opening is larger than two times a pitch width P of the plurality of turbine blades.

According to the fourth aspect of the invention, since the arc width W in the circumferential direction of the nozzle opening is larger than two times the pitch width P of the blades, the air injected from the nozzle opening always acts substantially on three or more turbine blades of the turbine blade portion. Therefore, the rotor can be smoothly rotated and a torque ripple can be reduced.

In a fifth aspect of the invention, an air turbine handpiece comprises a grip portion, a head portion disposed at a tip end of the grip portion, and a rotor having a turbine blade portion, disposed in a chamber formed in the head portion, the rotor being rotatably supported via bearing means, integrally with a rotation shaft, and a tool being detachably attached to the rotation shaft, wherein the turbine blade portion of the rotor has a hub and a plurality of turbine blades which are arranged on an outer peripheral surface of the hub in a circumferential direction at substantially regular intervals, each of the turbine blades has a first blade portion which extends in a substantially projected arcuate form in a rotation direction of the rotor and a second blade portion which is substantially continuous with the first blade portion and which extends in a direction separating from the first blade portion and in a direction opposite to the rotation of the rotor, a nozzle opening for injecting air toward the first blade portions of the turbine blades, and an exhaust opening for exhausting the air which has been injected toward the turbine blades, to an outside are opened to the chamber, and air which has been injected from the nozzle opening to the first blade portions of the turbine blades is guided by the first blade portions to flow in the direction opposite to the rotation direction, then guided by the second portions in the direction separating from the first blade portions and in the direction opposite to the rotation direction, and thereafter exhausted to the outside through the exhaust opening.

According to the fifth aspect of the invention, each of the turbine blades of the rotor has the first blade portion which extends in a substantially projected arcuate form in the rotation direction of the rotor and the second blade portion which is substantially continuous with the first blade portion and which extends in a direction separating from the first blade portion and in the direction opposite to the rotation direction of the rotor. The air from the nozzle opening is injected toward the first blade portions of the turbine blades. Therefore, the air injected from the nozzle opening flows in the direction opposite to the rotation direction along the arcuate surfaces of the first blade portions, and is then guided in the rotation direction along the second blade portions which are continuous with the first blade portions, so that air flows smoothly along the turbine blades. Therefore, air injected toward the turbine blade portion flows smoothly along the turbine blades and hardly functions as a resistance to the rotation, with the result that the rotor can be efficiently rotated.

In a sixth aspect of the invention, the hub of the turbine blade has a first portion having an outer peripheral surface which extends in a substantially recessed arcuate form in an inward radial direction of the rotor, and a second portion which extends from the first portion in a rotation axial direction of the rotor, and a part of the air injected from the nozzle opening is guided by the first and second portions of the hub and then directed toward the turbine blades.

According to the sixth aspect of the invention, since the hub of the turbine blade portion has the first portion having an outer peripheral surface which extends in substantially arcuate form in an inward radial direction of the rotor, and the second portion which extends from the first portion in the rotation axial direction of the rotor, a part of the air which is injected from the nozzle opening and which acts on the hub, is guided to the turbine blades along the first and second portions, and then acts on the turbine blades. As a result, the air contributes to generating the rotation torque of the rotor so that the rotation torque of the rotor can be increased.

In a seventh aspect of the invention, the first blade portions of the plurality of turbine blades are formed in the shape of circular arc having a radius of curvature which is 1.5 or more times the height H of the nozzle opening in the rotation axial direction.

According to the seventh aspect of the invention, since the first blade portion of each turbine blade is formed in the shape of circular arc having a radius of curvature which is 1.5 or more times the height H of the nozzle opening in the rotation axial direction, air injected from the nozzle opening toward the first blade portions is guided by the arcuate surfaces of the first blade portions so as to smoothly flow in the direction opposite to the rotation direction.

In an eighth aspect of the invention, the second blade portions of the plurality of turbine blades extend in the direction opposite to the rotation direction, inclined at an angle of 15 to 45 deg. with respect to a plane which is substantially perpendicular to the rotation axis of the rotor.

According to the eighth aspect of the invention, since the second blade portion of each turbine blade extends in the direction opposite to the rotation direction, inclined at an angle of 15 to 45 deg. with respect to a plane which is substantially perpendicular to the rotation axis of the rotor, air guided along the first blade portions is further guided along the second blade portions in a downward direction (and/or in an upward direction) in the direction opposite to the rotation direction. Therefore, air flows smoothly along the first and second blade portions contributes to generating the rotation torque. Since air flows smoothly, a velocity of the flow is less reduced. This allows the higher rotation torque to be obtained.

In a ninth aspect of the invention, the hub and the plurality of turbine blades of the turbine blade portion are integrally formed by synthetic resin molding, powder sintering, or metal injection molding.

According to the ninth aspect of the invention, since the turbine blade portion is formed by synthetic resin molding, powder sintering, or metal injection molding, the turbine blade portion can be produced relatively easily and economically.

In a tenth aspect of the invention, the hub and the plurality of turbine blades of the turbine blade portion are integrally formed by synthetic resin molding, and a cylindrical insert part is inserted into the hub, and projections and depressions for enhancing coupling between the hub and the insert part are formed on an outer peripheral surface of the insert part.

According to the tenth aspect of the invention, since the turbine blade portion is formed by synthetic resin molding and the insert part having projections and depressions on the surface is integrally insert-molded to the hub of the turbine blade portion, the turbine blade portion can be firmly fixed to the rotation shaft via the insert part. Since there are projections and depressions on the surface of the insert part, moreover, the turbine blade portion and the insert part can be firmly coupled to each other.

In an eleventh aspect of the invention, a synthetic resin material used in the synthetic resin molding is one of polyphenylene sulfide (PPS), fluororesin, polyether imide, polyether ether ketone, liquid crystal polymer, aromatic polyolefin, polycarbonate, and phenol resin.

According to the eleventh aspect of the invention, since the synthetic resin material used in the synthetic resin molding is one of the above-mentioned materials, a turbine blade portion which has sufficient strength and heat resistance can be obtained.

In a twelfth aspect of the invention, an arc width W in a circumferential direction of the nozzle opening which is opened to the chamber is larger than two times the height H in a rotation axial direction of the rotor.

According to the twelfth aspect of the invention, since the arc width W of the nozzle in the circumferential direction is larger than two times the height H in a rotation axial direction of the rotor, it is possible to cause the air injected from the nozzle opening to concentrically act on the center portions of the turbine blades in the axial direction. Furthermore, the nozzle opening can be ensured to have a large area so that the injection quantity of air can be increased.

In a thirteenth aspect of the invention, an air flow path which guides air to the nozzle opening is disposed in the head portion, and a partition wall which guides air to the nozzle opening is disposed in the air flow path.

According to the thirteenth aspect of the invention, since the partition wall is disposed in the air flow path which guides air to the nozzle opening, air flowing through the air flow path is guided by the partition wall. Therefore, it is possible to prevent air flowing through the air flow path from being biased.

In a fourteenth aspect of the invention, the head portion comprises a head body and a flow path member which cooperate with each other to form the chamber, the air flow path is formed between the head body and the flow path member by attaching the flow path member to the head body, and the partition wall is disposed on the flow path member.

According to the fourteenth aspect of the invention, since the air flow path is formed between the head body and the flow path member which is attached to the head body, the head portion having the air flow path can be produced relatively easily and economically. Since the partition wall is disposed on the flow path member, the partition wall can be easily disposed.

In a fifteenth aspect of the invention, a fitting hole which communicates with the air flow path is formed in one end portion of the flow path member, and one end of an air feed tube for feeding air is connected to the fitting hole.

According to the fifteenth aspect of the invention, since the end of the air feed tube is connected to the fitting hole, parts related to the flow path member can be easily assembled, and the air flow path and an air supply tube extending through the grip portion can be connected via the air feed tube. A connecting operation can be easily conducted.

In a sixteenth aspect of the invention, the flow path member is formed by plastic working, synthetic resin molding, or powder sintering.

According to the sixteenth aspect of the invention, since the flow path member is formed by plastic working, synthetic resin molding, or powder sintering, the flow path member can be produced relatively easily and economically.

In a seventh aspect of the invention, an air turbine handpiece comprises a grip portion, a head portion disposed at a tip of the grip portion, and a rotor disposed in a chamber formed in the head portion, the rotor being rotatably supported via bearing means, integrally with a rotation shaft, a tool being detachably attached to the rotation shaft, wherein the rotor has first and second turbine blade portions, a nozzle opening for injecting air toward the first turbine blade portion, and an exhaust opening for exhausting the injected air to an outside are opened to the chamber, air injected from the nozzle opening acts on the first turbine blade portion in a direction which is substantially perpendicular to the rotation axis of the rotor, is then guided from the first turbine blade portion to the second turbine blade portion, acts on the second turbine blade portion in a direction which is substantially perpendicular to the rotation axis of the rotor, and is thereafter exhausted from the second turbine blade portion to the outside through the exhaust opening.

According to the seventeenth aspect of the invention, the rotor has the first and second turbine blade portions, and air is injected from the nozzle opening toward the first turbine blade portion. The air injected from the nozzle acts on the first turbine blade portion and is then guided to the second turbine blade portion to act thereon. Thereafter, the air is exhausted to the outside through the exhaust opening. When the air from the first turbine blade portion acts on the second turbine blade portion, the flow velocity of the air is slightly lowered. Therefore, the air acts on the second turbine blade portion so as to increase the rotation torque of the blade portion and to slightly decrease a number of rotations. In this way, the rotation torque can be made larger without increasing the number of rotations. The air injected from the nozzle opening acts on the first turbine blade portion in a direction which is substantially perpendicular to the rotation axis of the rotor, and hence efficiently acts on the first turbine blade portion. Furthermore, the air guided to the second turbine blade portion acts on the second turbine blade portion in a direction which is substantially perpendicular to the rotation axis of the rotor, and hence efficiently acts on the second turbine blade portion.

In an eighteenth aspect of the invention, the first turbine blade portion of the rotor has a first hub and a plurality of first turbine blades which are arranged on an outer peripheral surface of the first hub in a circumferential direction at intervals, each of the first turbine blades has a first blade portion which extends in a substantially projected arcuate form in a rotation direction of the rotor, and a second blade portion which is substantially continuous with the first blade portion and which extends in a direction separating from the first blade portion and in a direction opposite to the rotation direction of the rotor, the second turbine blade portion has a second hub and a plurality of second turbine blades which are arranged on an outer peripheral surface of the second hub in the circumferential direction at intervals, each of the second turbine blades has a first blade portion which extends in a substantially projected arcuate form in the rotation direction of the rotor and a second blade portion which is substantially continuous with the first blade portion and which extends in a direction separating from the first blade portion and in a direction opposite to the rotation direction of the rotor, and air injected from the nozzle opening acts on the first blade portions of the first turbine blades of the first turbine blade portion, the air being guided by the first blade portions to flow in the direction opposite to the rotation direction, being further guided by the second blade portions of the first turbine blades in a direction separating from the first blade portions and in the direction opposite to the rotation direction, thereafter acting on the first blade portions of the second turbine blades of the second turbine blade portion being guided by the first blade portions in the direction opposite to the rotation direction, being further guided by the second blade portions of the second turbine blades in the direction opposite to the rotation direction, thereafter being exhausted to the outside through the exhaust opening.

According to the eighteenth aspect of the invention, the first and second turbine blade portions of the rotor have the first and second hubs, and the first and second turbine blades, respectively. Each of the first and second turbine blades has the first blade portion which extends in a projected arcuate form in the rotation direction of the rotor, and the second blade portion which is substantially continuous with the first blade portion and which extends in a direction separating from the first blade portion and in the direction opposite to the rotation direction. Therefore, air injected from the nozzle opening is guided by the first blade portions of the first turbine blade portion in the direction opposite to the rotation direction, guided by the second blade portions of the first turbine blades in a direction separating from the first blade portions and in the direction opposite to the rotation direction, guided by the first blade portions of the second turbine blade portion in the direction opposite to the rotation direction, and guided by the second blade portions of the second turbine blades in the direction opposite to the rotation direction. As a result, air flows smoothly through the first and second turbine blade portions and the air flow acts extremely less as rotation resistance.

In a nineteenth aspect of the invention, the first hub of the first turbine blade portion has a first portion having an outer peripheral surface which extends in a substantially recessed arcuate form in an inward radial direction of the rotor, and a second portion which extends from the first portion in a rotation axial direction of the rotor, and a part of the air injected from the nozzle opening is guided by the first and second portions of the first hub and then directed toward the first turbine blade portions of the first turbine blade portion.

According to the nineteenth aspect of the invention, since the first hub of the first turbine blade portion has the first portion which extends in a substantially arcuate form in an inward radial direction of the rotor, and the second portion which extends from the first portion in the rotation direction of the rotor, and a part of the air injected from the nozzle opening, which acts on the first hub, is guided to the first turbine blades along the first and second portions, and then acts on the first turbine blades. As a result, the air contributes to generating the rotation torque of the rotor so that the rotation torque of the rotor is increased.

In a twentieth aspect of the invention, the second hub of the second turbine blade portion has a first portion having an outer peripheral surface which extends in a substantially recessed arcuate form in an inward radial direction of the rotor, and a second portion which extends from the first portion in a rotation axial direction of the rotor, and a part of the air injected toward the second turbine blade portion is guided by the first and second portions of the second hub and then directed toward the second turbine blades of the second turbine blade portion.

According to the twentieth aspect of the invention, since the second hub of the second turbine blade portion has the first portion which extends in a substantially arcuate form in an inward radial direction of the rotor and the second portion which extends from the first portion in the rotation direction of the rotor, a part of the air which is guided from the first turbine blade portion and which acts on the second hub is guided to the second turbine blades along the first and second portions, and then acts on the second turbine blades. As a result, the air contributes to generating the rotation torque of the rotor so that the rotation torque of the rotor is further increased.

In a twenty-first aspect of the invention, the first blade portions of the first turbine blades of the first turbine blade portion of the rotor are formed into the shape of a circular arc having a radius of curvature which is 1.5 or more times the height H of the nozzle opening in the rotation axial direction.

According to the twenty-first aspect of the invention, since the first blade portions of the first turbine blades of the first turbine blade portion are formed in the shape of a circular arc having a radius of curvature which is 1.5 or more times the height H of the nozzle opening, air injected from the nozzle opening toward the first blade portion of the first turbine blade portion is guided by the arcuate surface of the first blade portion so as to smoothly flow in the direction opposite to the rotation direction.

In a twenty-second aspect of the invention, the second blade portions of the first and second turbine blade portions extend in the direction opposite to the rotation direction, inclined at an angle of 15 to 45 deg. with respect to a plane which is substantially perpendicular to the rotation axis of the rotor.

According to the twenty-second aspect of the invention, since the second blade portions of the first and second turbine blade portions of the rotor extend in the direction opposite to the rotation direction, inclined at an angle of 15 to 45 deg. with respect to a plane which is substantially perpendicular to the rotation axis of the rotor, air guided along the first blade portions of the first turbine blade portion is further guided along the second blade portions which is continuous to the first blade portions, in the direction opposite to the rotation direction toward the second turbine blade portion, and air guided along the first blade portions of the second turbine blade portion is further guided along the second blade portions which is continuous to the first blade portions, in the direction opposite to the rotation direction. Therefore, air flows smoothly from the first blade portions to the second blade portions in each of the first and second turbine blade portions, and air is injected in the direction opposite to the rotation direction. Therefore, air flowing from the first blade portions to the second blade portions in each of the first and second turbine blade portions contributes to generating the rotation torque. Since air flows smoothly, the velocity of the flow is less reduced. This also allows the rotation torque to be further increased.

In a twenty-third aspect of the invention, the head portion comprises a head body which forms the chamber, an inner housing member is attached to an interior of the chamber of the head body, a sleeve member is attached to an outer peripheral surface of the inner housing member, and an auxiliary air flow path which guides air from the first turbine blade portion to the second turbine blade portion is formed by the sleeve member and the inner housing member.

According to the twenty-third aspect of the invention, since the auxiliary air flow path is formed by the inner housing member and the sleeve member attached to the outer peripheral surface of the member, air from the first turbine blade portion is surely guided to the second turbine blade portion by the auxiliary air flow path.

In a twenty-fourth aspect of the invention, a plurality of flow path openings are disposed in the inner housing member in a circumferential direction at intervals, and the sleeve member is attached to the inner housing member so as to cover the plurality of flow path openings, thereby the flow path openings function as the auxiliary air flow path, and air from the first turbine blade portion is introduced from one end of each of the flow path openings and then injected toward the second turbine blade portion from other ends of the flow path openings.

According to the twenty-fourth aspect of the invention, the plurality of flow path openings are formed in the inner housing member, air from the first turbine blade portion is introduced from one end of each of the flow path openings, and the air flowing through the flow path openings are injected toward the second turbine blade portion from the other ends of the openings so that the air is surely injected toward a predetermined area of the second turbine blade portion.

In a twenty-fifth aspect of the invention, the inner housing member and/or the sleeve member are formed by metal injection molding, powder sintering, or synthetic resin molding.

According to the twenty-fifth aspect of the invention, since the inner housing member and/or the sleeve member are formed by metal injection molding, powder sintering, or synthetic resin molding, the inner housing member and/or the sleeve member can be produced relatively easily and economically.

In a twenty-sixth aspect of the invention, the first and second turbine blade portions of the rotor are integrally formed by synthetic resin molding, powder sintering, or metal injection molding.

According to the twenty-sixth aspect of the invention, the rotor having the first and second turbine blade portions can be produced relatively easily and economically.

In a twenty-seventh aspect of the invention, the first and second turbine blade portions of the rotor are integrally formed by synthetic resin molding, and a cylindrical insert part is inserted across the first and second turbine blade portions, and projections and depressions for enhancing coupling of the portions are formed on an outer peripheral surface of the insert part.

According to the twenty-seventh aspect of the invention, since the first and second turbine blade portions are integrally formed by synthetic resin molding and the insert part is inserted across the first and second turbine blade portion portions, the rotor can be firmly fixed to the rotation shaft via the insert part. Since there are projections and depressions on the surface of the insert part, moreover, the rotor and the insert part can be firmly coupled to each other.

In a twenty-eighth aspect of the invention, a synthetic resin material used in the synthetic resin molding is one of polyphenylene sulfide (PPS), fluororesin, polyether imide, polyether ether ketone, liquid crystal polymer, aromatic polyolefin, polycarbonate, and phenol resin.

According to the twenty-eighth aspect of the invention, since the above-mentioned synthetic resin material is used as the material of the first and second turbine blade portions, the turbine blade portions can have sufficient strength and heat resistance.

BRIEF DESCRIPTION OF THE DRAWINGS

Other and further objects, features, and advantages of the invention will be more explicit from the following detailed description taken with reference to the drawings wherein:

FIG. 4 is a perspective view showing separated head body and flow path member of the handpiece of FIG. 1;

DETAILED DESCRIPTION OF THE PREFERRED EMBODIMENTS

Figure 1:
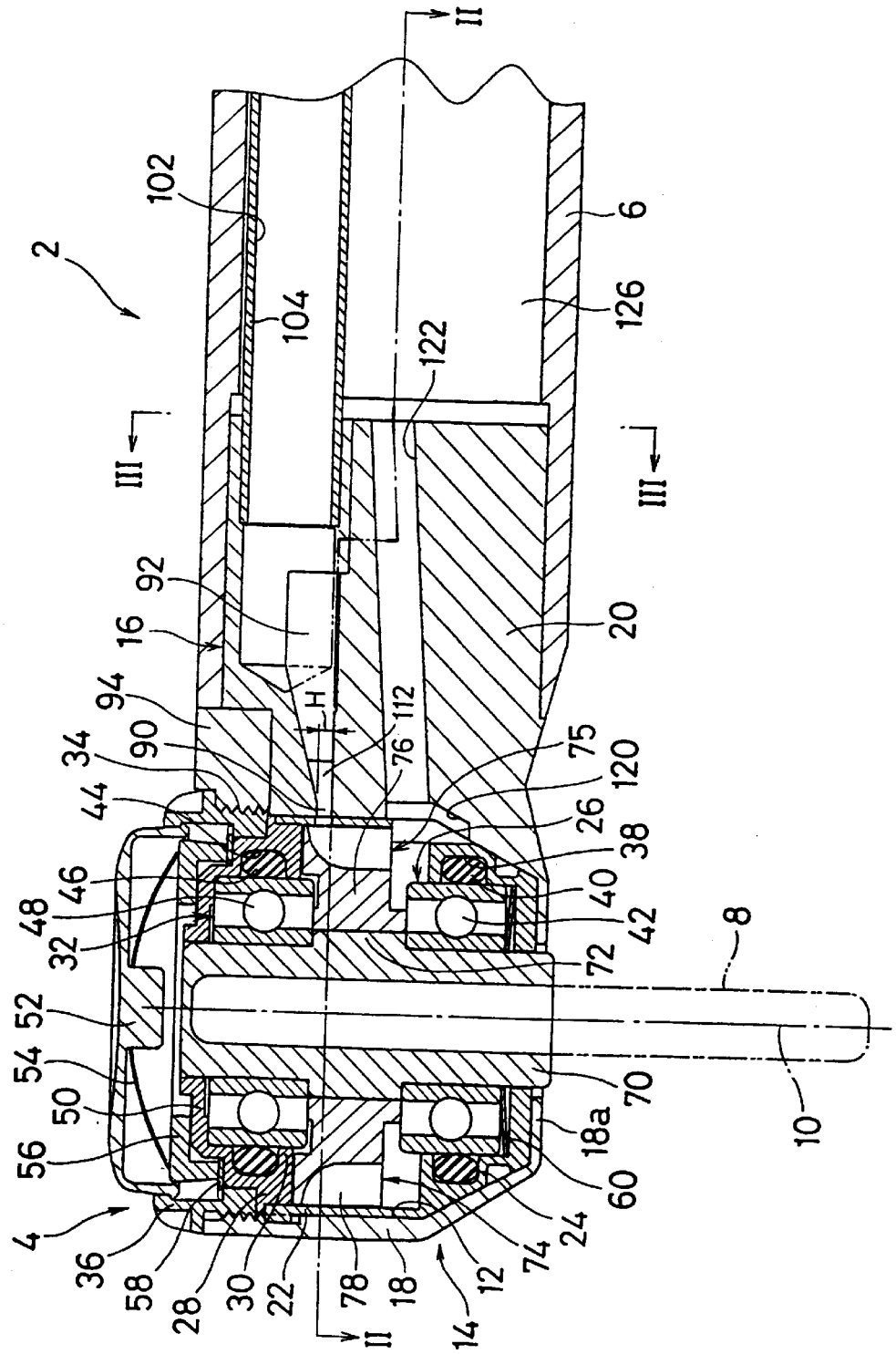
FIG. 1 is a partial section view showing main portions of a first embodiment of an air turbine handpiece of the invention.

Now referring to the drawings, preferred embodiments of the invention are described below.

Figure 2:
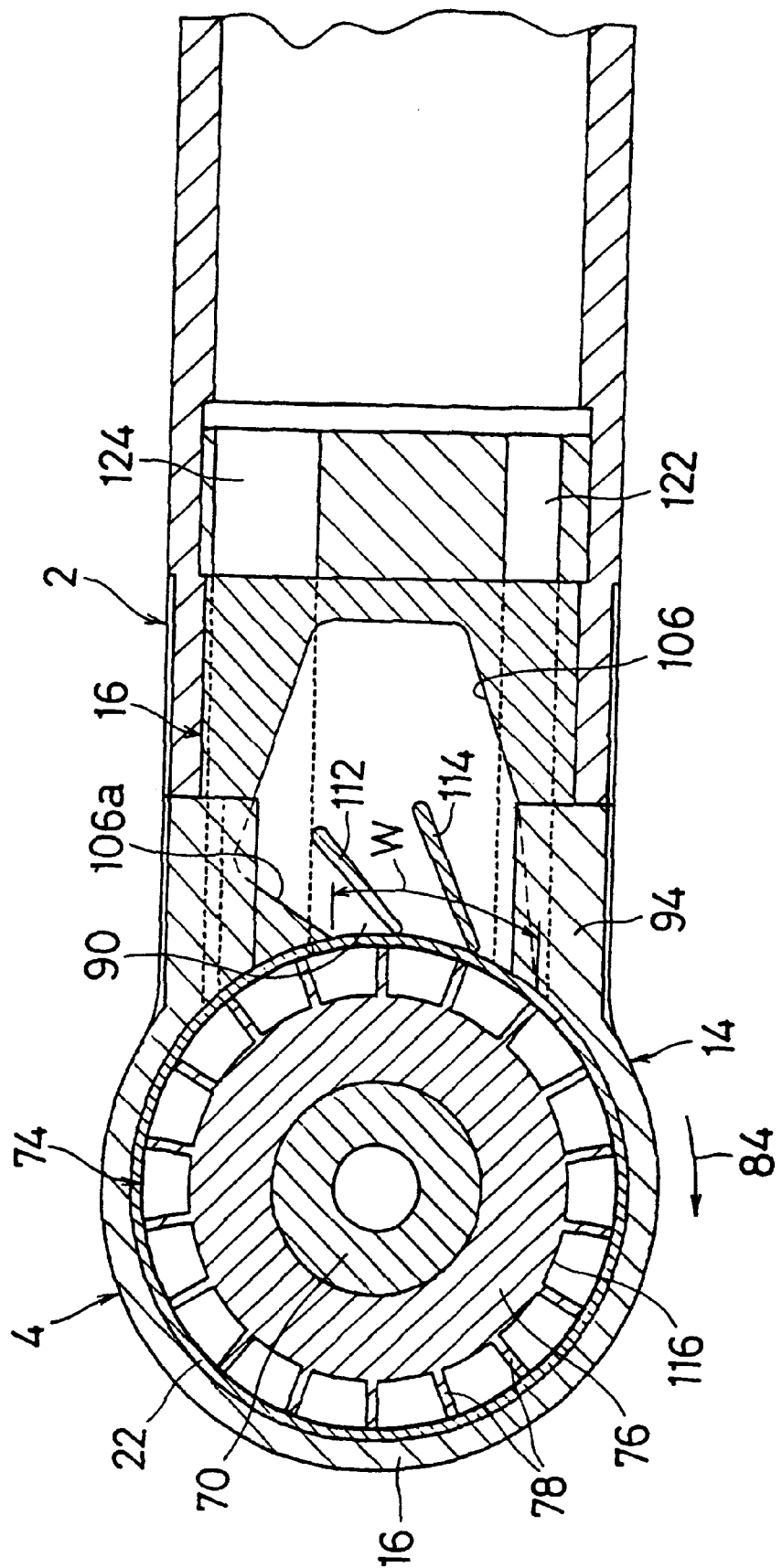
FIG. 2 is a section view taken along a line II—II of FIG. 1.
Figure 3:
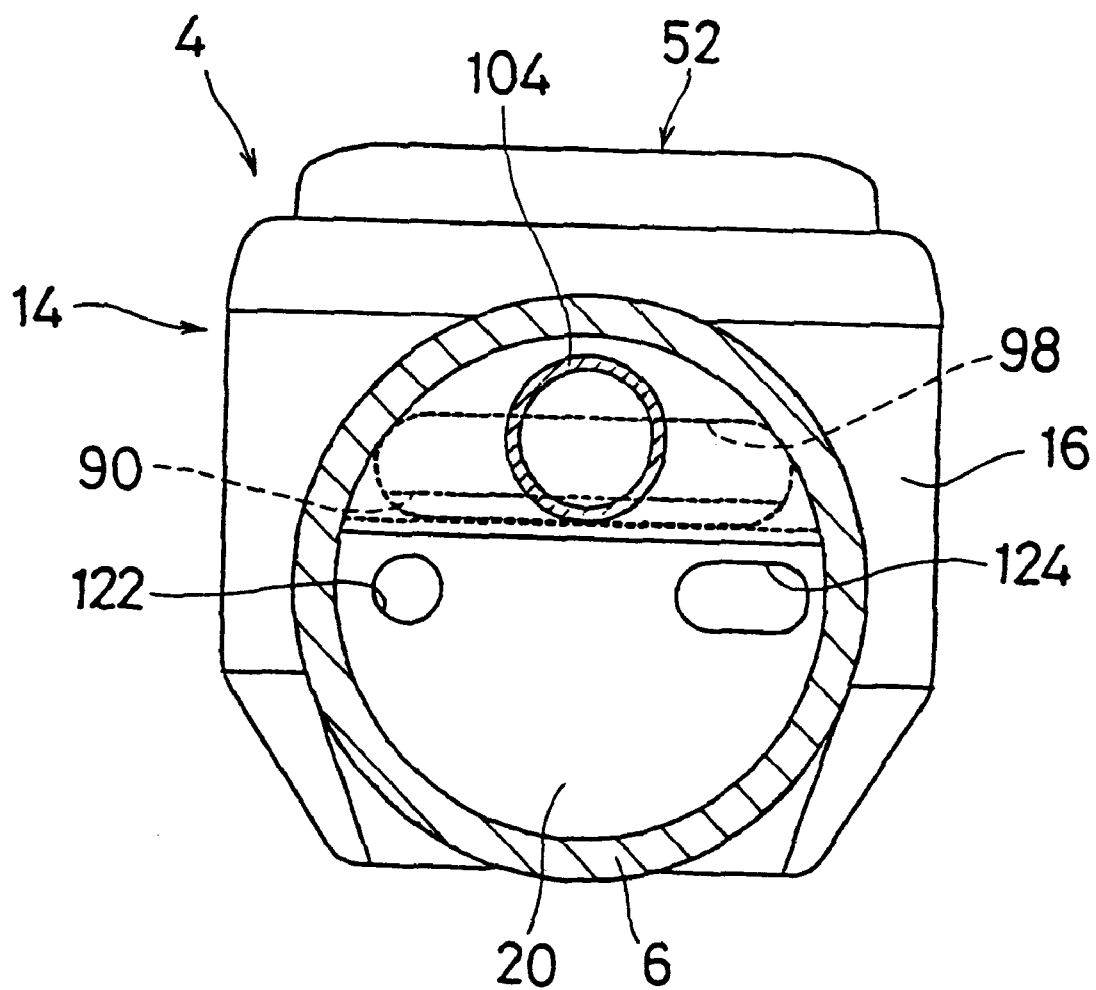
FIG. 3 is a section view taken along a line III—III of FIG. 1.

Hereinafter, the invention will be described further in detail with reference to the accompanying drawings. FIG. 1 is an enlarged section view showing a portion of a first embodiment of the air turbine handpiece of the invention, FIG. 2 is a section view taken along a line II—II of FIG. 1, and FIG. 3 is a section view taken along a line III—III of FIG. 1. Hereinafter, embodiments in which the handpiece of the invention is used in the dental treatment will be described. However, the invention is not limited to this and may be applied to other fields, for example, surgical treatment or cutting work for usual materials, parts, or the like.

Referring to FIGS. 1 to 3, the illustrated handpiece which can be advantageously used in, for example, dental treatment comprises a grip portion 2 and a head portion 4 which is disposed at a tip of the grip portion 2. An operator holds the grip portion 2 and conducts, for example, cutting work of teeth. As shown in FIG. 1, in the handpiece of the embodiment, the grip portion 2 has a grip body 6 which is substantially cylindrical. A rotation axis 10 of a dental cutting tool 8 which is attached to the head portion 4 (the rotation axis 10 also functions as a rotation axis of a rotor and a rotation shaft described later) extends in a direction which is substantially perpendicular to an axis (extending laterally in FIG. 1) of the grip body 6. Such a handpiece in which the rotation axis 10 of the dental cutting tool 8 extends in this way is called a contra-angle handpiece.

In the first embodiment, the head portion 4 comprises a head body 14 having a cylindrical chamber 12, and a flow path member 16 attached to the head body 14. The head body 14 is configured by a body portion 18 which is substantially cylindrical, and a connecting portion 20 which is projected from the body portion 18 toward the grip body 6. An inner housing member 22 is attached to an interior of the chamber 12 formed in the body portion 18, so as to extend along an inner surface of the body portion 18. An annular bearing support 24 is disposed at one end portion of the inner housing member 22, and one ball bearing 26 is attached to the bearing support 24. A bearing support member 28 is attached to the other end portion of the inner housing member 22, and another ball bearing 32 is attached to an annular bearing support 30 disposed on the bearing support member 28. In the embodiment, a female thread is disposed in an upper end opening of the body portion 18. An annular flange 34 which is projected in an outward radial direction is disposed on an outer peripheral surface of the bearing support member 28. The annular flange 34 is placed on the other end surface of the inner housing member 22 and a male thread disposed on a clamping member 36 is screwed in the female thread of the body portion 18, thereby the inner housing member 22 and the bearing support member 28 are held between an end wall 18a of the body portion 18 and the clamping member 36.

In the embodiment, furthermore, an annular recess 38 is disclosed on the inner peripheral surface of the bearing support 24 of the inner housing member 22. A ring 40 made of rubber is attached to the annular recess 38. A portion of the ball bearing 26 where a ball 42 is disposed is supported via the ring 40. An annular recess 44 is formed in the inner peripheral surface of the bearing support 30 of the bearing support member 28. A ring 46 made of rubber is attached to the annular recess 44 as well. A portion of the other ball bearing 32 where a ball 48 is disposed is supported via the ring 46. An annular abutting portion 50 which is projected in an inward radial direction is disposed on the bearing support member 28. The annular abutting portion 50 acts on the outer race of the other ball bearing 32.

A pressing member 52 for opening and closing chucking means (not illustrated) attached to a rotation shaft 70, a dish-shaped spring member 54, and a sleeve member 56 are disposed on an outside (the upper side in FIG. 1) of the bearing support member 28. The pressing member 52 is attached to the clamping member 36, the sleeve member 56 abuts against a plate-shaped member 58 attached to the clamping member 36, and the spring member 54 is interposed between the sleeve member 56 and the pressing member 52. A dish-shaped spring 60 for pre-loading the ball bearings 26 and 32 is interposed between the ball bearing 26 and the inner housing member 22.

The rotation shaft 70 is rotatably supported by the pair of ball bearings 26 and 32 (constituting bearing means). A large-diameter portion 72 is integrally disposed in a middle portion of the rotation shaft 70. The pair of ball bearings 26 and 32 are disposed on an outside of the large-diameter portion 72. For example, the dental cutting tool 8 is detachably attached to the rotation shaft 70 via the chucking means which is not illustrated, as indicated by a tow-dot chain line in FIG. 1. The chucking means can be opened and closed by pressing the pressing member 52. A rotor 74 for rotating the cutting tool 8 is fixed to the outer peripheral surface of the large-diameter portion 72 of the rotation shaft 70 by means of press fitting or the like.

Figure 6:
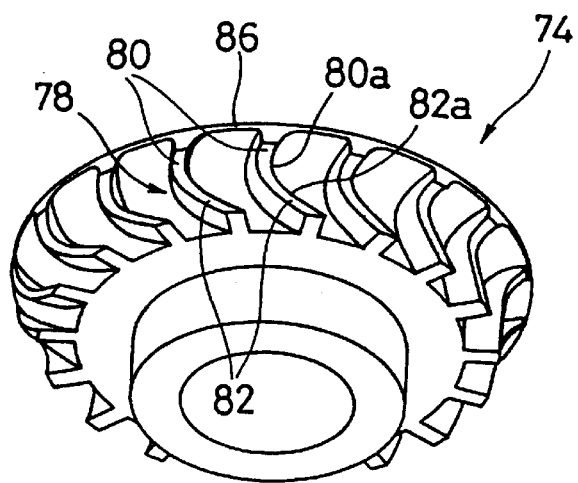
FIG. 6 is a perspective view showing a rotor of the handpiece of FIG. 1.
Figure 7:
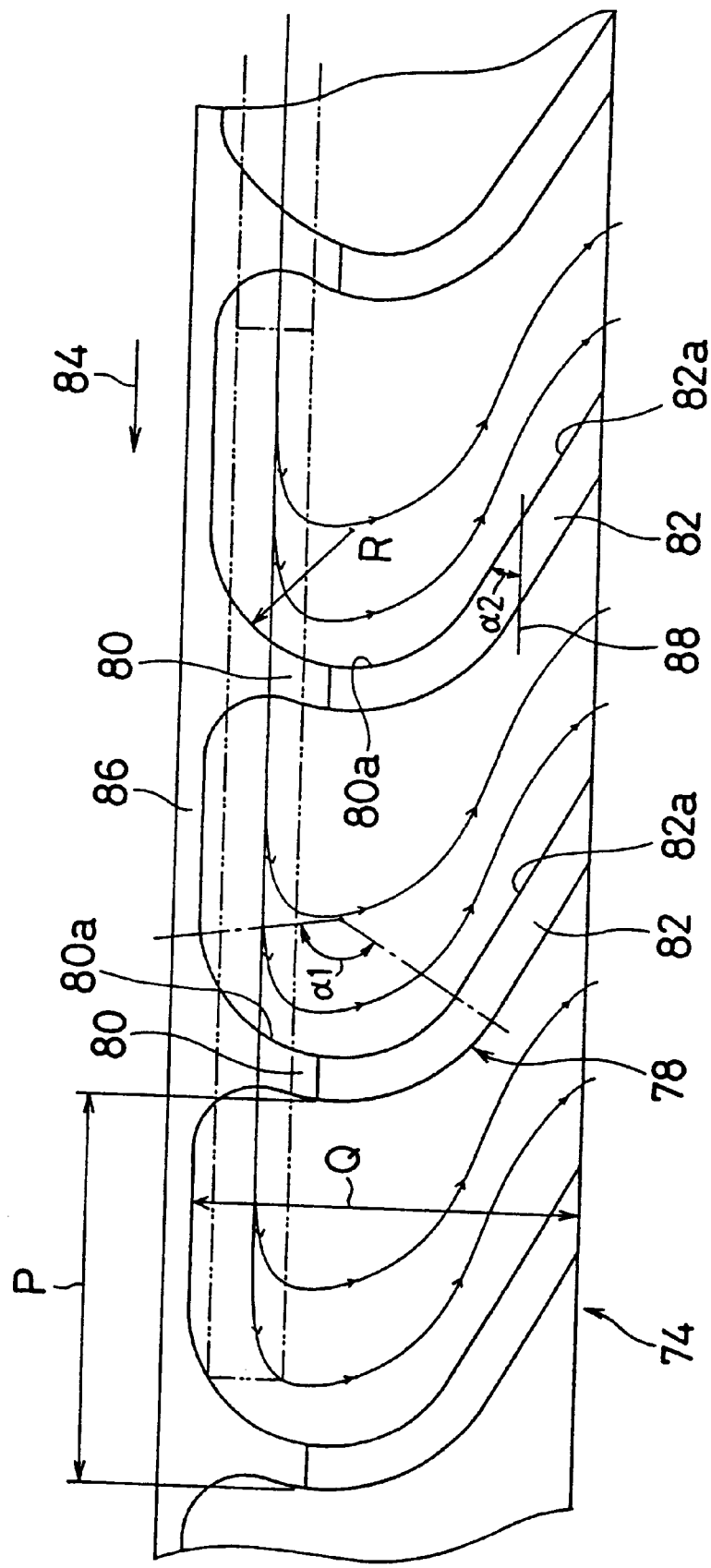
FIG. 7 is a development view showing turbine blades of FIG. 6.

The rotor will be further described with reference to FIG. 6 which is a perspective view of the rotor, and FIG. 7 which is a development view of the rotor, in addition to FIGS. 1 and 2. The illustrated rotor 74 has a turbine blade portion 75. The turbine blade portion 75 is configured by a hub 76 which is substantially cylindrical, and a plurality of (in the embodiment, 18) turbine blades 78 which are arranged on the outer peripheral surface of the hub 76 in the circumferential direction at substantially regular intervals. The turbine blades 78 have a substantially same shape, and each of the blades comprises a first blade portion 80 which extends in a substantially projected arcuate form in the rotation direction of the rotor 74, i.e., vertically and arcuately in FIGS. 1 and 7, and a second blade portion 82 which linearly extends so as to be continuous with the first blade portion 80. Right surfaces of the first and second blade portions 80 and 82 in FIG. 7, i.e., the surfaces which are on the rear side in the rotation direction indicated by an arrow 84 in FIGS. 2 and 7 function as the operating surfaces to which air is injected. The first blade portions 80 are projected in the rotation direction indicated by the arrow 84. According to this configuration, the operating surfaces 80a are recessed. In the embodiment, an end wall 86 is disposed in one end portion (the upper end portion) of the turbine blade portion 75, and the first blade portions 80 extend from the end wall 86. The first blade portions 80, more particularly their operating surfaces 80a extends arcuately from the end wall 86 in a semicircular form over an angle range of 120 to 150 deg. A region indicated by an angle α1 in FIG. 7 serves as the first blade portion 80. The second blade portions 82, more particularly, their operating surfaces 82a extend in the direction opposite to the rotation direction, inclined at a predetermined angle α2 with respect to a plane 88 which is substantially perpendicular to the rotation axis 10 of the rotor 74. Preferably, the predetermined angle α2 is 15 to 45 deg. When the inclination angle α2 of each second blade portion 82 is set in this way, air guided from the first blade portions 80 to the second blade portions 82 flows smoothly, and also the air which flows along the second blade portions 82 in the direction opposite to the rotation direction contributes to generating the rotation torque, so as to obtain increased rotation torque. Since air flows smoothly, a velocity of the flow is less reduced and it is possible to obtain further increased rotation torque.

In the turbine blade portion 75, since the end wall 86 is disposed at the one end of the portion, air injected as described later does not substantially flow toward the one end, and is guided by the first and second blade portions 80 and 82 so as to flow toward the other end of the turbine blade portion 75. In the embodiment, in order to cause the above-mentioned air to flow further smoothly, as shown in FIGS. 1 and 6, an upper portion of the hub 76, i.e., the outer peripheral surface of the first portion extends downward from the upper end in a substantially recessed arcuate form in an inward radial direction, and the lower portion, i.e., the outer peripheral surface of the second portion downward extends in parallel with the rotation axis 10 of the rotor 74 or vertically. According to this configuration, air injected toward the hub 76 is guided to the turbine blade 78 along the first and second portions of the hub and then acts on the turbine blades 78 to contribute to generating the rotation torque of the rotor 74. This also allows the rotation torque of the rotor 74 to be further increased.

In the rotor 74, preferably, the hub 76 and the plurality of turbine blades 78 are integrally formed. Such a rotor can be produced relatively easily and economically by synthetic resin molding, powder sintering, or metal injection molding. In the case where the rotor is formed by synthetic resin molding, polyphenylene sulfide (PPS), fluororesin, polyether imide, polyether ether ketone, liquid crystal polymer, aromatic polyolefin, polycarbonate, phenol resin, or the like is favorably used as the resin material. When the rotor is made of such a resin material, the rotor can have sufficient rigidity and heat resistance as a dental handpiece. When the hub 76 and the turbine blades 78 are integrally molded using a synthetic resin, a metal insert part (not illustrated) which is cylindrical may be inserted into the hub 76. In this case, the hub 76 of the rotor 74 is coupled to the rotation shaft 70 via the insert part, and hence the rotor 74 and the rotation shaft 70 can be firmly coupled to each other. When the insert part is to be insert-molded, it is preferable to form projections and depressions on the surface of the insert part. The formation of projections and depressions enhances the coupling between the insert part and the hub 76 of the rotor 74.

Figure 5:
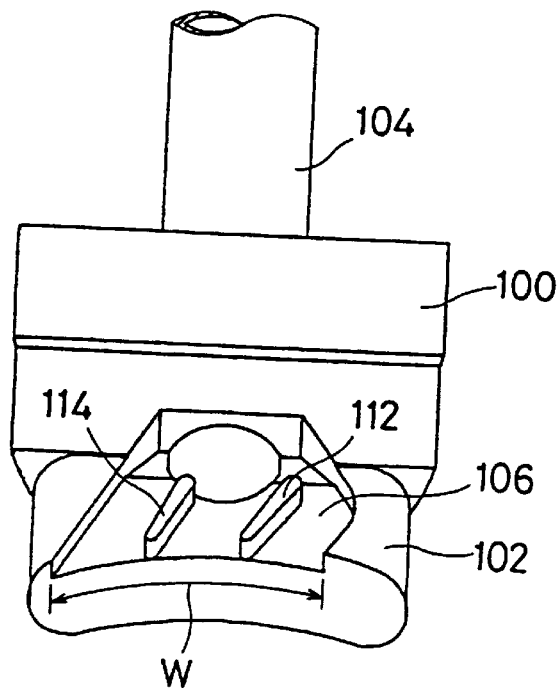
FIG. 5 is a perspective view showing the flow path member of the handpiece of FIG. 1 as seen from a lower side.

Referring to FIGS. 3 to 5 together with FIGS. 1 and 2, a nozzle opening 90 which is approximately rectangular is opened to the chamber 12 of the head portion 4. The nozzle opening 90 opposes the one end (the upper end) of the first blade portion 80 of the turbine blade portion 75 and is opened in a direction which is substantially perpendicular to the rotation axis 10 of the rotor 74. An air flow path 92 extends from the nozzle opening 90 toward the grip body 6. In the embodiment, as shown in FIG. 4, the connecting portion 20 extends from the body portion 18 of the head body 14 via a cylindrical neck portion 94. The connecting portion 20 has a semicylindrical shape in which the upper surface is approximately flat. In the upper portion of the neck portion 94, a slot 98 which is laterally flat in FIG. 4 extends toward the chamber 12. By contrast, the flow path member 16 comprises a semicylindrical portion 100 in which the lower surface is approximately flat, and a projection 102 which extends from one end surface of the semicylindrical portion 100. The flow path member 16 is attached to the head body 14 by inserting the projection 102 into the slot 98 and placing the semicylindrical portion 100 on the connecting portion 20. When the flow path member 16 is attached in this way, the connecting portion 20 of the head body 14, and the semicylindrical portion 100 of the flow path member 16 define a cylindrical surface. As shown in FIG. 1, the connecting portion 20 of the head body 14, and the semicylindrical portion 100 of the flow path member 16 are inserted into the tip of the grip body 6 to be attached thereto.

In the embodiment, as shown in FIGS. 1, 2, and 5, a fitting hole 103 (FIG. 1) is disposed in the other end of the semicylindrical portion 100 of the flow path member 16, and one end of an air feed tube 104 is connected to the fitting hole 103. Although not illustrated, an air supply tube connected to an air supply source is incorporated in the grip body 6, and the tip of the air supply tube is connected to the other end of the air feed tube 104. When the air feed tube 104 is attached in this way, a configuration relating to the flow path member 16 can be simplified, and the connection between the flow path member 16 and the air supply tube (not illustrated) is facilitated. As shown in FIGS. 1, 2, and 5, a recess 106 which communicates with the fitting hole 102 is formed in the lower surface of the flow path member 16. An arc width of the recess 106, i.e., the circumferential width of the recess 106, in the rotation direction of the rotor 74, gradually increases toward the tip of the projection 102 and then tapers toward the nozzle opening 90. The recess 106 functions as an air flow path 92 which guides air from the air feed tube 104 to the nozzle opening 90. When the flow path member 16 is attached to the head body 14, the air flow path 92 is formed between the components.

The configuration relating to the recess 106, i.e., the air flow path 92 is formed as follows. A surface of the recess 106 (the surface opposing the connecting portion 20 of the head body 14) is linearly inclined so as to approach the connecting portion 20 of the head body 14 as moving toward the nozzle opening 90, whereby a height of the air flow path 92 in the direction of the rotation axis 10 is gradually reduced toward the nozzle opening 90. Since the height of the air flow path 92 is gradually reduced toward the nozzle opening 90 in this way, a pressure of air flowing through the air flow path 92 is raised as flowing toward the nozzle opening 90, with the result that the compressed air of a raised pressure is injected from the nozzle opening 90 toward the turbine blade portion 75.

In the air flow path 92, two partition walls 112 and 114 are separately disposed in the width direction of the flow path, i.e., the width direction along the rotation direction of the turbine blade portion 75. The partition walls 112 and 114 are formed integrally with the flow path member 16, and projected from the above-described surface of the recess 106 toward the neck portion 94 of the head body 14. As shown in FIG. 2, each of the partition walls 112 and 114 is slightly tapered toward the end. According to this configuration, the end portion of the air flow path 92 is divided into three portions by the partition walls 112 and 114. Air from these portions flows along the partition walls 112 and 114, then injected toward the turbine blades 78 of the rotor 74. This partition enables air from the air feed tube 104 to be substantially uniformly dispersed without being biased in the width direction of the nozzle opening 90. Therefore, air is substantially uniformly injected from the nozzle opening 90 toward the rotor 74. The partition walls 112 and 114 are not always necessary. When air can be uniformly injected from the nozzle opening 90, the partition walls 112 and 114 may be omitted.

It is desirable that a size of the nozzle opening 90 is set, for example, in the following manner. An arc width W (FIGS. 2 and 4) in the circumferential direction of the nozzle opening 90, i.e., the width along the circumferential direction of the turbine blade portion 75 is set to be two or more times a height H (FIGS. 1 and 5) in the direction of the rotation axis 10 of the rotor 74 (W≧2 H). More desirably, the arc width W in the circumferential direction is set to be 5 to 20 times the height H in the rotation axial direction (5 H≦W≦20 H), and, further desirably, set to be 7 to 15 times the height H in the rotation axial direction (7 H≦W≦15 H). When the size of the nozzle opening 90 is set in this way, the arc width W of the opening in the circumferential direction is larger than the height H in the rotation axial direction, and it is possible to ensure a sufficiently large opening area for the nozzle opening while holding down the height H of the nozzle opening 90. As a result, a sufficient quantity of air can be injected from the nozzle opening 90. When the embodiment is used as a dental handpiece, the arc width W of the nozzle opening 90 is set to be about 3 to 6 mm and the height H of the nozzle opening 90 is set to be about 0.3 to 0.6 mm.

Preferably, the arc width W in the circumferential direction of the nozzle opening 90 is set to be larger than 2 times a pitch width P (FIG. 7) of the turbine blades 78 of the turbine blade portion 75 (W>2 P). According to this setting, the air injected from the nozzle opening 90 always acts substantially on three or more turbine blades 78 of the turbine blade portion 75. Therefore, the rotor 74 can be smoothly rotated and a torque ripple can be reduced. Preferably, the height H of the nozzle opening 90 is set to be ⅕ to ⅓ time the width Q (FIG. 7) of the turbine blade 78 of the turbine blade portion 75 in the direction of the rotation axis 10 of the rotor 74 (⅕ Q≦H≦⅓ Q). According to this setting, the air injected from the nozzle opening 90 toward the turbine blade portion 75 does not widely spread in the direction of the rotation axis 10 of the turbine blade portion 75 and is concentrically injected toward a predetermined part of the turbine blade portion 75, with the result that the injected air efficiently acts on the turbine blades 78. In order to cause the air to smoothly flow from the first blade portions 80 of the turbine blade portion 75 to the second blade portions 82, it is desirable that a radius of curvature R (FIG. 7) of each first blade portion 80, more particularly each arcuate operating surface 80a is set to be 1.5 or more times the height H of the nozzle opening 90 in the direction of the rotation axis 10 (R≧1.5 H).

It is desirable that the flow path member 16 which defines a part of the nozzle opening 90 is formed by plastic working, synthetic resin molding, or powder sintering. When the member is formed by such a processing method, the flow path member 16 of a complicated shape can be produced relatively easily and economically. As a resin material used in the synthetic resin molding, for example, one of polyphenylene sulfide (PPS), fluororesin, polyether imide, polyether ether ketone, liquid crystal polymer, aromatic polyolefin, polycarbonate, phenol resin, or the like can be preferably used. Also it is a matter of course that the flow path member 16 may be formed by a cutting work with an end mill or the like.

An exhaust opening 120 is opened to the chamber 12 of the head portion 4. In the embodiment, the exhaust opening 120 is disposed below the position where the turbine blade portion 75 is disposed. Air injected from the nozzle opening 90 toward the turbine blade portion 75 is guided down toward the exhaust opening 120 by the first and second blade portions 80 and 82 of the turbine blades 78 in the direction opposite to the rotation direction. The width in the circumferential direction of the exhaust opening 120 is set so as to be lager than the arc width W in the circumferential direction of the nozzle opening 90. Therefore, the air injected from the nozzle opening 90 acts on the turbine blade portion 75 and then efficiently guided to the exhaust opening 120. Exhaust flow paths 122 and 124 are formed so as to pass through the neck portion 94 and the connecting portion 20 of the head body 14. One end of each of the exhaust flow paths 122 and 124 communicates with the exhaust opening 120. The other ends of the exhaust flow paths 122 and 124 are connected to an air exhaust flow path 126 which is defined in the grip body 6. Air is exhausted to the outside through the air exhaust flow path 126. In the embodiment, the two exhaust flow paths 122 and 124 are disposed in the connecting portion 20 of the head body 14. Alternatively, the exhaust flow paths 122 and 124 may be replaced with a single exhaust flow path of a large cross-sectional area.

In the embodiment, as seen from FIG. 1, openings which respectively correspond to the nozzle opening 90 and the exhaust opening 120 and which are slightly larger than these openings are formed in the inner housing member 22. Therefore, the air from the nozzle opening 90 is injected into the chamber 12 through the corresponding opening, and the air injected into the chamber 12 is guided to the exhaust opening 120 through the corresponding opening of the inner housing member 22.

Referring mainly to FIGS. 1 and 2, an operation of the handpiece will be described. The driving air from the air supply source (not illustrated) is supplied to the air flow path 92 of the flow path member 16 through the air supply tube (not illustrated) incorporated in the grip body 6, and then injected from the nozzle opening 90 toward the turbine blades 78 of the turbine blade portion 75. The air injected from the nozzle opening 90 is guided by the partition walls 112 and 114. Although the nozzle opening 90 has the large arc width in the circumferential direction, therefore, the air is prevented from being biased in the width direction, and injected substantially uniformly in the width direction of the nozzle opening 90.

The air injected from the nozzle opening 90 acts on the operating surfaces of the turbine blades 78 of the turbine blade portion 75. Specifically, the air acts on the operating surfaces 80a of the first blade portions 80 of the turbine blades 78, and flows along the operating surfaces 80a in the direction opposite to the rotation direction indicated by the arrow 84 (FIG. 2), and further flows along the operating surfaces 82a of the second blade portions 82 in a direction separating from the first blade portions 80 and in the direction opposite to the rotation direction. In this way, the air injected from the nozzle opening 90 flows smoothly downward in the direction opposite to the rotation direction as indicated by solid lines with arrows in FIG. 7. Consequently, the injected air is prevented from becoming a rotation resistance to the turbine blade portion 75. Furthermore, the velocity of the air flow is less reduced and also the air flowing along the second blade portions 82 contributes to generating the rotation torque, with the result that high rotation torque can be obtained. The air flowing along the turbine blades 78 of the turbine blade portion 75 is guided to the exhaust opening 120 and then passes from the exhaust opening 120 through the exhaust flow paths 122 and 124 and the air exhaust flow path 126 to be exhausted to the outside.

In this way, the rotor 74 is continuously rotated by the air which is supplied from the air supply source (not illustrated), passes through the chamber 12, and is then exhausted to the outside. A rotation of the rotor 74 causes the rotation shaft 70 and the dental cutting tool 8 attached thereto to rotate in a predetermined direction. The rotated cutting tool 8 is made to act on a tooth to be treated, thereby cutting the tooth. In the embodiment, air is caused to efficiently act on the turbine blade portion 75, and hence it is possible to obtain high rotation torque. Consequently, a large cutting force can be obtained by a small air supply quantity. This is effective also in miniaturization of the handpiece, particularly, the head portion 4.

The first embodiment described above has the configuration in which the air injected from the nozzle opening 90 is guided downward along the operating surface of the turbine blade portion 75 in the direction opposite to the rotation direction. In place of this configuration, the handpiece may be configured so that air is guided upward in the direction opposite to the rotation direction, or upward and downward in the direction opposite to the rotation direction. In such a case, the second blade portions 82 are disposed so as to extend upward from the upper end of the first blade portion 80 of each turbine blade 78 in the direction opposite to the rotation direction, and, in accordance with this disposition, the exhaust opening 120 is placed above the nozzle opening 90. Alternatively, the second blade portions 82 are disposed so as to extend upward and downward from the upper and lower end portions of the first blade portion 80 of each turbine blade 78 in the direction opposite to the rotation direction, and, in accordance with this disposition, the exhaust opening 120 is placed above and below the nozzle opening 90.

The handpiece is provided with a water supply flow path and an air supply flow path for injecting water and/or air toward a diseased part to be treated, and a configuration associated with the flow paths. In FIGS. 1 to 7 showing the first embodiment, these components are omitted.

Figure 8:
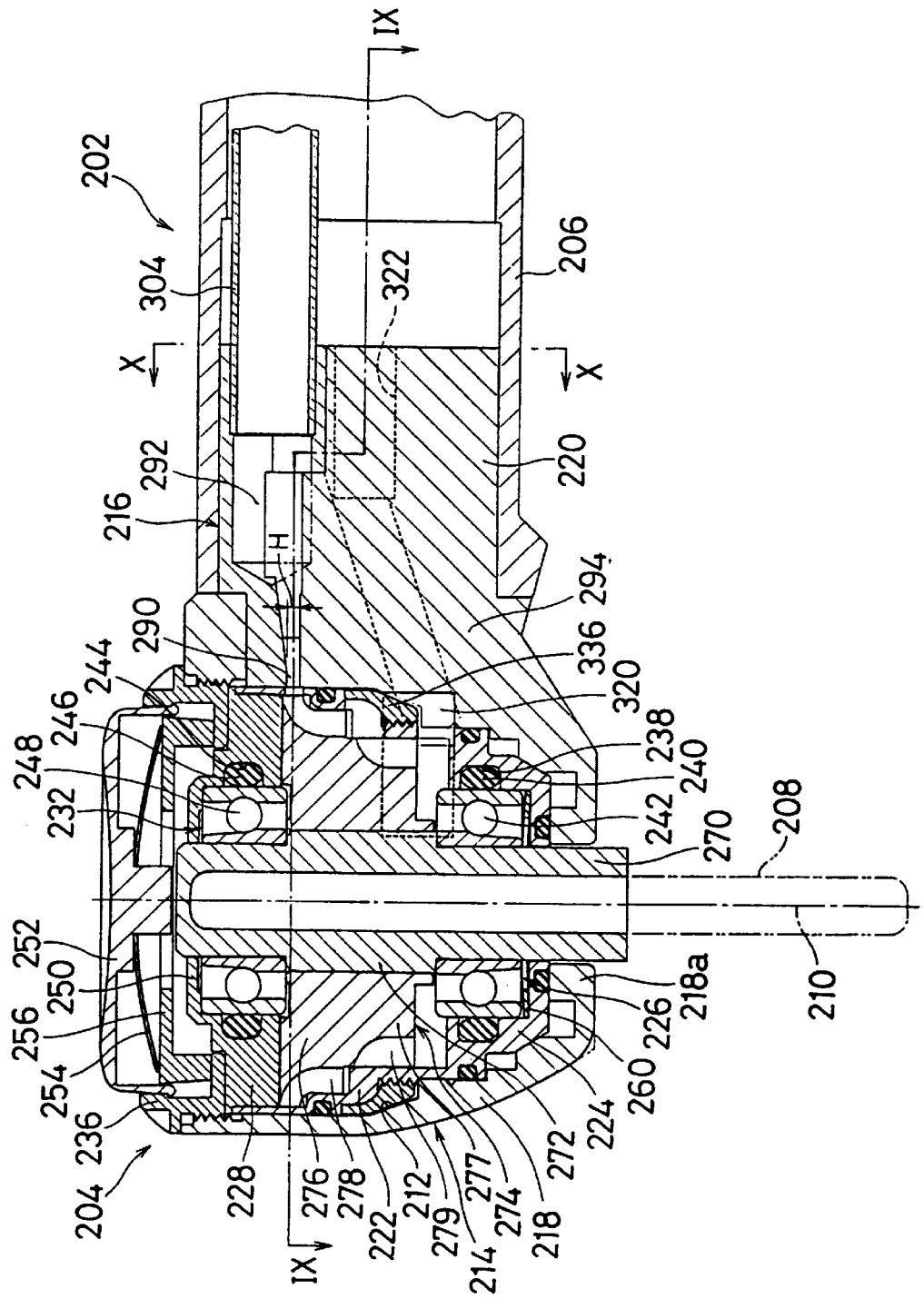
FIG. 8 is a partial section view showing main portions of a second embodiment of the air turbine handpiece of the invention.

Next, a second embodiment of the air turbine handpiece of the invention will be described. FIG. 8 is an enlarged section view showing a part of the second embodiment of the air turbine handpiece of the invention, FIG. 9 is a section view taken along a line IX—IX of FIG. 8, and FIG. 10 is a section view taken along a line X—X of FIG. 8.

Figure 9:
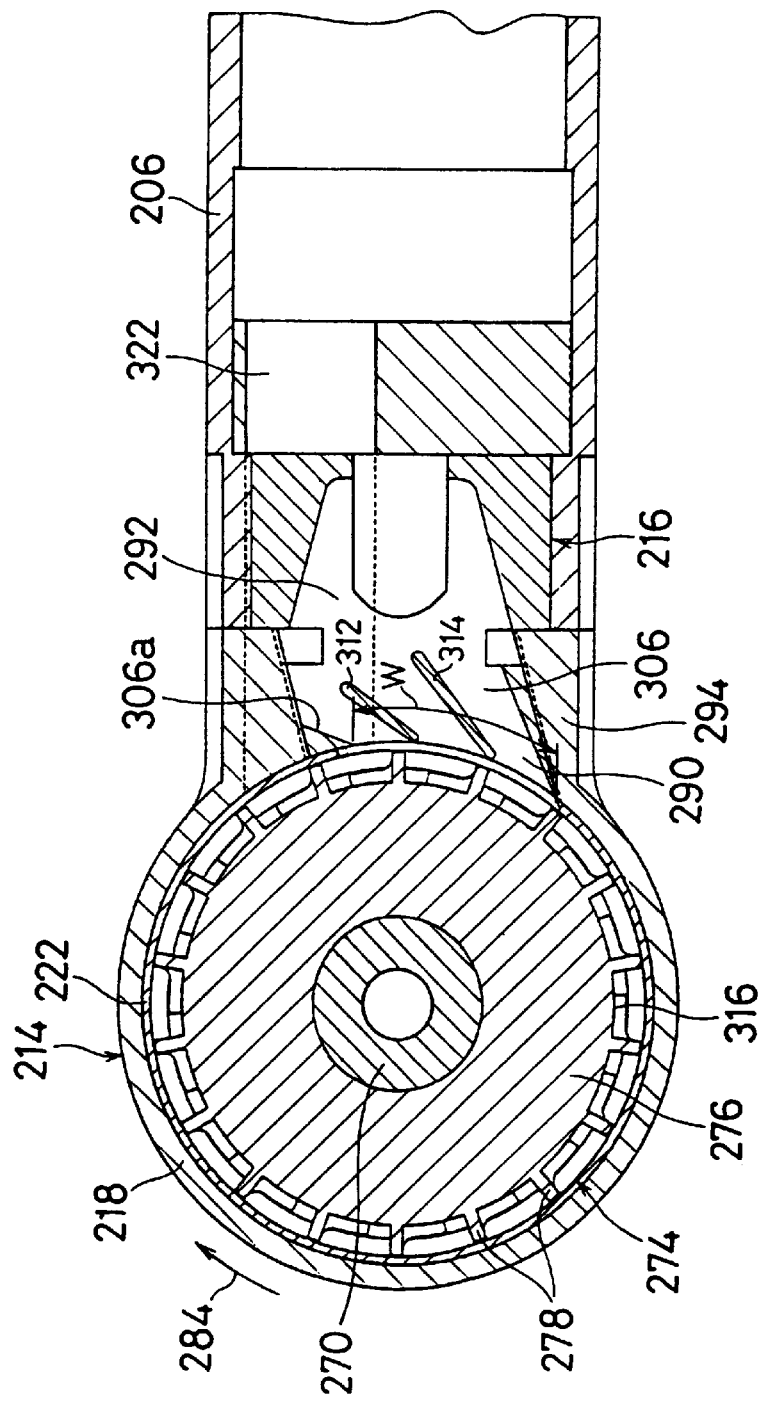
FIG. 9 is a section view taken along a line IX—IX of FIG. 8.
Figure 10:
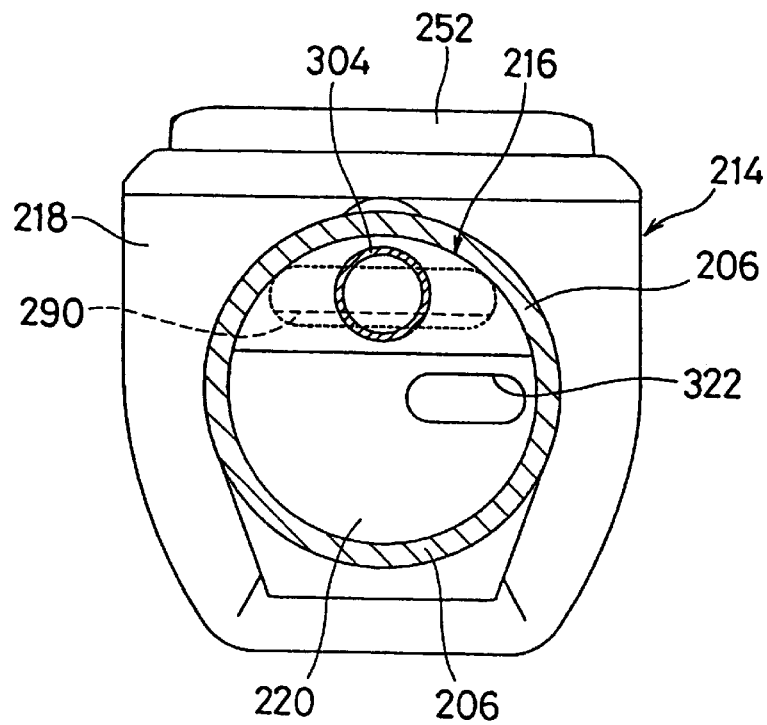
FIG. 10 is a section view taken along a line X—X of FIG. 8.

Referring to FIGS. 8 to 10, the illustrated handpiece which can be preferably used, for example, in dental treatment comprises a grip portion 202 and a head portion 204 which is disposed at a tip of the grip portion 202. An operator holds the grip portion 202 and conducts, for example, a cutting work of teeth. Also the handpiece of the second embodiment is of the contra-angle type. As shown in FIG. 8, the grip portion 202 has a grip body 206 which is substantially cylindrical. A rotation axis 210 of a dental cutting tool 208 which is attached to the head portion 204 (the rotation axis also 210 functions as a rotation axis of a rotor and a rotation shaft described later) extends in a direction which is substantially perpendicular to an axis (extending laterally in FIG. 8) of the grip body 206.

Also in the second embodiment, the head portion 204 comprises a head body 214 having a cylindrical chamber 212, and a flow path member 216 which is attached to the head body 214. The head body 214 is configured by a body portion 218 which is substantially cylindrical, and a connecting portion 220 which is projected from the body portion 218 toward the grip body 206. An inner housing member 222 is attached to an interior of the chamber 212 formed in a body portion 218, so as to extend along an inner surface of the body portion 218. An annular bearing support 224 is disposed at one end portion of the inner housing member 222, and one ball bearing 226 is attached to the bearing support 224. A bearing support member 228 is attached to the other end portion of the inner housing member 222, and another ball bearing 232 is attached to the bearing support member 228. In the embodiment, a female thread is formed in an upper end opening of the body portion 218. An annular flange 234 which is projected in an outward radial direction is disposed on an outer peripheral surface of the bearing support member 228. The annular flange 234 is placed on the other end surface of the inner housing member 222 and a male thread disposed on a clamping member 236 are screwed with the female thread of the body portion 218, thereby holding the inner housing member 222 and the bearing support member 228 between an end wall 218a of the body portion 218 and the clamping member 236.

In the second embodiment, an annular recess 238 is disposed on an inner peripheral surface of the bearing support 224 of the inner housing member 222. A ring 240 made of rubber is attached to the annular recess 238. Therefore, a portion of the ball bearing 226 where a ball is disposed is supported via the ring 240. An annular recess 244 is disposed on an inner peripheral surface of the bearing support 228. A ring 246 made of rubber is attached to the annular recess 244. Therefore, a portion of the ball bearing 232 where a ball 248 is disposed is supported via the ring 246. An annular recess 244 is formed in the inner peripheral surface of the bearing support member 228. An annular abutting portion 250 which is projected in an inward radial direction is disposed on the bearing support member 228. The annular abutting portion 250 acts on an outer race of the ball bearing 232.

A pressing member 252 for opening and closing chucking means (not illustrated) attached to a rotation shaft 270, a dish-shaped spring member 254, and a sleeve member 256 are disposed on an outside of the bearing support member 228, i.e., the upper side in FIG. 8. The pressing member 252 is attached to the clamping member 236, the sleeve member 256 abuts against the clamping member 236, and the spring member 254 is interposed between the pressing member 252 and the sleeve member 256. A dish-shaped spring 260 for preloading the ball bearings 226 and 232 is interposed between the ball bearing 226 and the inner housing member 222.

A rotation shaft 270 is rotatably supported by the pair of ball bearings 226 and 232 which constitute the bearing means. A large-diameter portion 272 is integrally disposed in a middle portion of the rotation shaft 270. The pair of ball bearings 226 and 232 are disposed on an outside of the large-diameter portion 272. In the same manner as the first embodiment, for example, the dental cutting tool 208 is detachably attached to the rotation shaft 270 via the chucking means which is not illustrated, as indicated by the tow-dot chain line in FIG. 8. The chucking means can be opened by pressing the pressing member 252 so as to replace the cutting tool 208 with another one. A rotor 274 for rotating the cutting tool 208 is fixed to an outer peripheral surface of the large-diameter portion 272 of the rotation shaft 270 by means of press fitting or the like.

Figure 14:
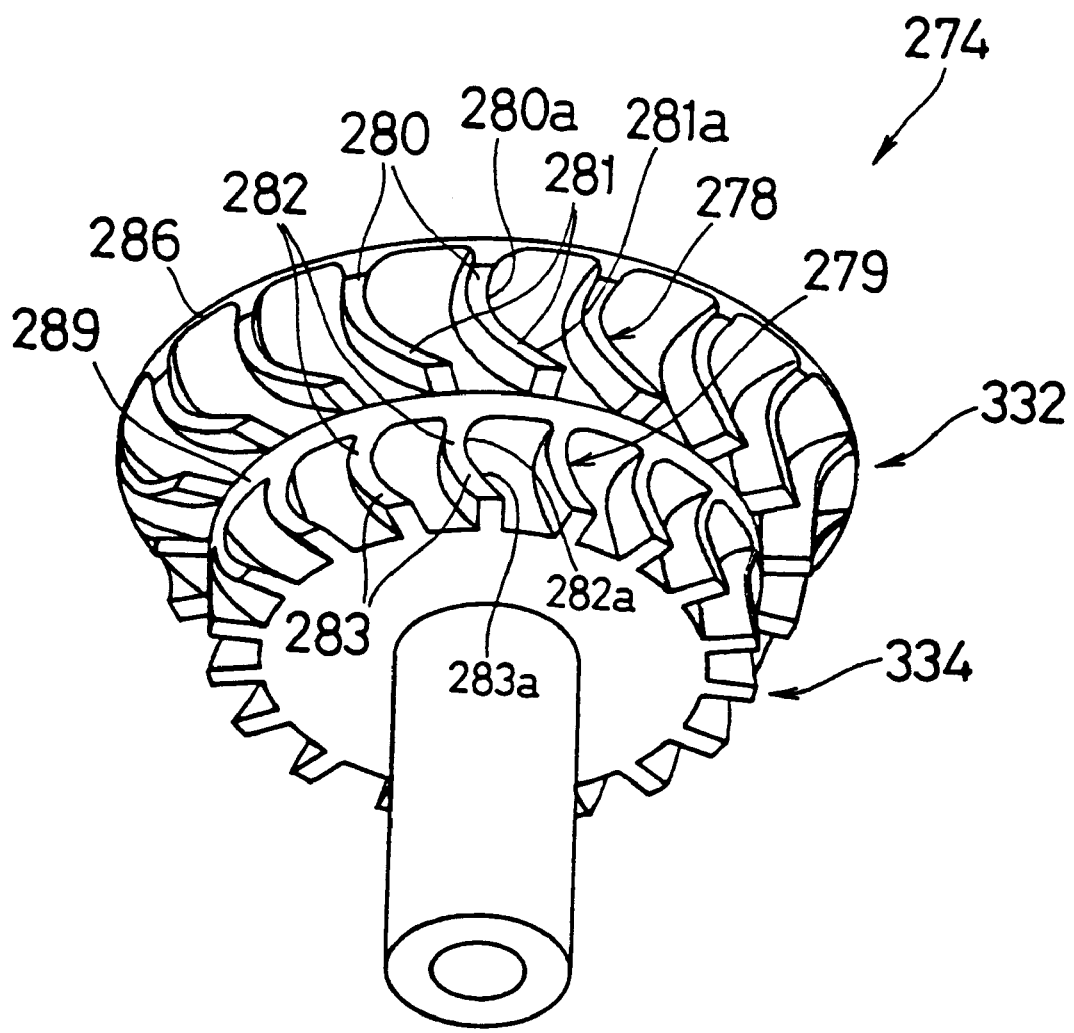
FIG. 14 is a perspective view showing the rotor of the handpiece of FIG. 8.

The rotor will be further described with reference to FIG. 14 which is a perspective view of the rotor, and FIG. 15 which is a development view of the rotor, in addition to FIGS. 8 and 9. The illustrated rotor 274 has a first turbine blade portion 332 which is disposed on one end (the upper end) of the rotor 274, and a second turbine blade portion 334 which is disposed on the other end (the lower end) of the rotor. The first turbine blade portion 332 is configured by a first hub 276 which is substantially cylindrical, and a plurality of (in the embodiment, 18) first turbine blades 278 which are arranged on an outer peripheral surface of the first hub 276 in the circumferential direction at substantially regular intervals. The plurality of first turbine blades 278 have a substantially same shape, and each of them comprises a first blade portion 280 which extends in a substantially projected arcuate form in the rotation direction of the rotor 274, i.e., the vertical directions in FIGS. 8 and 15, and a second blade portion 281 which linearly extends so as to be continuous with the first blade portion 280. Right surfaces of the first and second blade portions 280 and 281 in FIG. 15, i.e., the surfaces which are on a rear side in the rotation direction indicated by the arrow 284 in FIGS. 9 and 15 function as operating surfaces to which air is injected. The first blade portions 280 are projected in the rotation direction indicated by the arrow 284. According to this configuration, operating surfaces 280a are recessed. In the second embodiment, an end wall 286 is disposed in one end portion (the upper end portion) of the rotor 274, and the first blade portions 280 extend from the end wall 286. The first blade portions 280, more particularly their operating surfaces 280a arcuately extend from the end wall 286 in a semicircular shape over an angle range of 120 to 150 deg. A region which is indicated by an angle α3 in FIG. 15 serves as the first blade portion 280 of the first turbine blade 278. The second blade portions 281, more particularly their operating surfaces 281a of the portion extend in the direction opposite to the rotation direction, inclined at a predetermined angle α4 with respect to a plane 288 which is substantially perpendicular to the rotation axis 210 of the rotor 274. Preferably, the predetermined angle α4 is 15 to 45 deg. When the inclination angle α4 of the second blade portion 281 of each first turbine blade 278 is set in this way, air guided from the first blade portions 280 to the second blade portions 281 flows smoothly, and the flow velocity of the air is prevented from being lowered. As a result, it is possible to obtain further increased rotation torque. Also the air which flows along the second blade portion 281 contributes to generating the rotation torque. This also enables increased rotation torque to be obtained. In the rotor 274, since the end wall 286 is disposed at the one end of the rotor, air which is injected as described later does not substantially flow toward the one end, and is guided by the first and second blade portions 280 and 281 of the first turbine blades 278 so as to flow toward the second turbine blade portion 334.

Also in the embodiment, in order to cause the above-mentioned air to flow further smoothly, as shown in FIG. 8, the upper portion of the first hub 276, i.e., the outer peripheral surface of the first portion extends downward from the upper end in a recessed arcuate form in an inward radial direction, and the lower portion, i.e., the outer peripheral surface of the second portion extends downward in parallel with the rotation axis 210 of the rotor 274. Therefore, also air acting on the first hub 276 smoothly flows from the first portion to the second portion. The air flowing from the first portion to the second portion acts on the first turbine blades 278. This also allows the rotation torque to be further increased.

The second turbine blade portion 334 is disposed below an intermediate wall 289. The second turbine blade portion 334 has an outer diameter which is slightly smaller than that of the first turbine blade portion 332, and is configured in a substantially same manner as the first turbine blade portion 332. Specifically, the second turbine blade portion 334 is configured by a second hub 277 which is substantially cylindrical, and a plurality of (in the embodiment, 18) second turbine blades 279 which are arranged on an outer peripheral surface of the second hub 277 in the circumferential direction at substantially regular intervals. The second turbine blades 279 have a substantially same shape, and each of the blades comprises a first blade portion 282 which extends in a substantially projected arcuate form in the rotation direction of the rotor 274, and a second blade portion 283 which linearly extends so as to be continuous with the first blade portion 282. Right surfaces of the first and second blade portions 282 and 283 in FIG. 15, i.e., the surfaces which are on the rear side in the rotation direction indicated by the arrow 284 in FIG. 15 function as operating surfaces to which air is injected. In the first blade portion 282 of each second turbine blade 279, the upper portion, i.e., a part facing the first turbine blade portion 332 extends in the direction of the rotation shaft 210 of the rotor 274, or vertically and substantially linearly, and the lower portion is projected in the rotation direction indicated by the arrow 284. According to this configuration, the operating surfaces 282a are recessed. In the second turbine blade portion 334, the first blade portions 282 extend from intermediate wall 289, and the first blade portions 282, more particularly the arcuate portions of their operating surfaces 282a extend over an angle range of 50 to 70 deg. A region which is indicated by an angle α5 in FIG. 15 serves as an arcuately extending portion of the first blade portion 282 of the second turbine blade 279. As a result of this configuration, the air acting on the first blade portions 282 of the second turbine blades 279 flows downward along the operating surfaces 282a and is then guided in the direction opposite to the rotation direction as indicated by solid lines with arrows in FIG. 15. In accordance with the air flow from the first turbine blades 278, the first blade portions 282 of the second turbine blades 279 may have a shape which is substantially identical with that of the first blade portions 280 of the first turbine blades 278. The second blade portions 283, more particularly their operating surfaces 283a extend in the direction opposite to the rotation direction, inclined at a predetermined angle α6 with respect to a plane 331 which is substantially perpendicular to the rotation axis 210 of the rotor 274. Preferably, the predetermined angle α6 is 15 to 45 deg. in the same manner as that of the second blade portion 281 of each first turbine blades 278. When the inclination angle α6 of each second blade portion 283 is set in this way, air guided from the first blade portions 282 to the second blade portion 283 also flows smoothly in the second turbine blades 279, and increased rotation torque is obtained in the same manner as described above. In the rotor 274, since an intermediate wall 289 is disposed, air which is injected from the first turbine blade portion 332 to the second turbine blade portion 334 does not substantially flow toward the intermediate wall 289, and is guided by the first and second blade portions 282 and 283 of the second turbine blades 279 so as to be directed downward in the direction opposite to the rotation direction.

Also in the second turbine blade portion 334, in order to cause the above-mentioned air to flow further smoothly, as shown in FIG. 8, the upper portion of the second hub 277, i.e., the outer peripheral surface of the first portion extends downward from the upper end in a substantially recessed arcuate form in an inward radial direction, and the lower portion, i.e., the outer peripheral surface of the second portion extends downward in parallel with the rotation axis 210 of the rotor 274. Therefore, air acting on the second hub 277 flows smoothly from the first portion to the second portion. The air flowing from the first portion to the second portion acts on the second turbine blades 279. This also allows the rotation torque to be further increased.

In the above-described rotor 274, the first turbine blade portion 332 is disposed below the end wall 286, and the second turbine blade portion 334 is disposed below the first turbine blade portion 332 via the intermediate wall 289. Therefore, a height of the rotor 274 can be reduced. As a result of this configuration, the head portion 204 can be miniaturized.

In the rotor 274, it is desirable that the first turbine blade portion 332, specifically, the first hub 276 and the first turbine blades 278, and the second turbine blade portion 334, specifically, the second hub 277 and the second turbine blades 279 are integrally formed. Such a rotor can be produced relatively easily and economically by synthetic resin molding, powder sintering, or metal injection molding. It is a matter of course that the rotor 274 may be also formed by a cutting work. In the case where the rotor is formed by synthetic resin molding, polyphenylene sulfide (PPS), fluororesin, polyether imide, polyether ether ketone, liquid crystal polymer, aromatic polyolefin, polycarbonate, phenol resin, or the like is preferably used as the resin material. When the rotor is made of such a resin material, the rotor can have sufficient rigidity and heat resistance for a dental handpiece. When the first and second turbine blade portions 332 and 334 are integrally molded by using a synthetic resin, a metal insert part (not illustrated) which is cylindrical may be inserted into the first and second hubs 276 and 277. In this case, the first and second hubs 276 and 277 of the rotor 274 are coupled to the rotation shaft 270 via the insert part, and hence the rotor 274 and the rotation shaft 270 can be firmly coupled to each other. When the insert part is to be insert-molded, it is preferable to dispose projections and depressions on a surface of the insert part. The disposition of projections and depressions enhances the coupling between the insert part and the first and second hubs 276 and 277 of the rotor 274.

Referring to FIG. 10 together with FIGS. 8 and 9, a narrow nozzle opening 290 which is approximately rectangular is opened in the chamber 212 of the head portion 204. The nozzle opening 290 opposes one end (the upper end portion) of each first blade portion 280 of the first turbine blade portion 332 of the rotor 274 and is opened in a direction which is substantially perpendicular to the rotation axis 210 of the rotor 274. An air flow path 292 extends from the nozzle opening 290 toward the grip body 206. In the second embodiment, the connecting portion 220 extends from the body portion 218 of the head body 214 via a cylindrical neck portion 294 in the same manner as the first embodiment. The flow path member 216 is attached to the neck portion 294 and the connecting portion 220. As a result, the air flow path 292 is formed between the connecting portion 220 of the head body 214, and the flow path member 216. Configurations relating to the air flow path 292, i.e., the configurations of the neck portion 294 and the connecting portion 220 of the head body 214, and the flow path member 216 are substantially identical with those of the first embodiment. Therefore, detailed descriptions of these components are omitted.

In the embodiment, as shown in FIGS. 8 to 10, one end of an air feed tube 304 is connected to the flow path member 216. Although not illustrated, an air supply tube connected to an air supply source is incorporated in the grip body 206, and a tip of the air supply tube is connected to other end of the air feed tube 304. Therefore, compressed air from the air supply source is supplied to the air flow path 292 through the air supply tube.

In the air flow path 292, two partition walls 312 and 314 are separately disposed in a width direction of the flow path, i.e., the width direction along the rotation direction of the rotor 274. The partition walls 312 and 314 are integrally formed on the flow path member 216. The partition walls 312 and 314 are configured in a substantially same manner as those of the first embodiment, and are slightly tapered. Consequently, the end portion of the air flow path 292 is divided into three portions by the partition walls 312 and 314. Air from these portions flows along the partition walls 312 and 314 and then injected toward the first turbine blades 278 of the first turbine blade portion 332. This partition enables air from the air feed tube 304 to be substantially uniformly dispersed without being biased in the width direction of the nozzle opening 290. Therefore, air is injected from the nozzle opening 290 toward the first turbine blade portion 332 in a substantially uniform manner. When air can be uniformly injected from the nozzle opening 290, the partition walls 312 and 314 may be omitted.

In the same manner as the first embodiment, it is desirable that a size of the nozzle opening 290 is set in the following manner. The arc width W (FIG. 9) in the circumferential direction of the nozzle opening 290 is set to be 2 or more times the height H (FIG. 8) in the direction of the rotation axis 210 of the rotor 274 (W≧2 H). More desirably, the arc width W in the circumferential direction is set to be 3 to 20 times the height H in the rotation axial direction (3H≦W≦20 H), and, further desirably, set to be 7 to 15 times the height H (7 H≦W≦15 H). When the size of the nozzle opening 290 is set in this way, the arc width W of the opening in the circumferential direction is larger than the height H of the opening in the axial direction, and it is possible to ensure a sufficiently large opening area while holding down the height H of the nozzle opening 290. When the ratio between the arc width W and the height H is set as described above, the air from the nozzle opening 290 can be injected more efficiently to the first turbine blade portion 332. When the handpiece is used as a dental handpiece, the arc width W of the nozzle opening 290 is set to be about 3 to 6 mm and the height H of the nozzle opening 290 is set to be about 0.3 to 0.6 mm.

Preferably, the arc width W in the circumferential direction of the nozzle opening 290 is set to be larger than 2 times the pitch width P1 (FIG. 15) of the first turbine blades 278 of the first turbine blade portion 332 (W>2 P). According to this setting, the air injected from the nozzle opening 290 always acts substantially on three or more first turbine blades 278 of the first turbine blade portion 332. Therefore, the first turbine blade portion 332 can be smoothly rotated and the torque ripple can be reduced. Preferably, the height H of the nozzle opening 290 is set to be ⅕ to ⅓ of the width Q (FIG. 15) of the first turbine blades 278 of the first turbine blade portion 332 in the axial direction (⅕ Q≦H≦⅓ Q). According to this setting, the air injected from the nozzle opening 290 toward the first turbine blade portion 332 does not widely spread in the direction of the rotation axis 210 of the first turbine blade portion 332 and is concentrically injected toward a predetermined part of the first turbine blade portion 332, with the result that the injected air efficiently acts on the first turbine blade portions 278. In order to cause the air to smoothly flow from the first blade portions 280 of the first turbine blade portions 278 of the first turbine blade portion 332 to the second blade portions 281, the radius of curvature R (FIG. 15) of the first blade portion 280, more particularly the arcuate operating surfaces 280a are set to be 1.5 or more times the height H of the nozzle opening 290 in the axial direction (R≧1.5 H).

An exhaust opening 320 is opened, below the nozzle opening 290, to the chamber 212 of the head portion 204. In the second embodiment, the exhaust opening 320 is disposed below the position where the second turbine blade portion 334 of the rotor 274 is disposed. Air injected from the nozzle opening 290 toward the first turbine blade portion 332 of the rotor 274 is guided to the first and second blade portions 280 and 281 of the first turbine blade portions 278 and then guided downward in the direction opposite to the rotation direction, and then guided by the first and second blade portions 282 and 283 of the second turbine blade portions 279 of the second turbine blade portion 334 toward the exhaust opening 320 as described later. An arc width in the circumferential direction of the exhaust opening 320 is set so as to be above the arc width W in the circumferential direction of the nozzle opening 290. Also a height of the exhaust opening 320 is set so as to be above the height H of the nozzle opening. Therefore, the air injected from the nozzle opening 290 acts on the rotor 274 and is then efficiently guided to the exhaust opening 320.

In the second embodiment, an exhaust flow path 322 (FIG. 10) is formed so as to pass through the neck portion 294 and the connecting portion 220 of the head body 214. One end of the exhaust flow path 322 communicates with one side of the exhaust opening 320. The other end of the exhaust flow path 322 is connected to an air exhaust flow path 326 which is defined in the grip body 206. Air is exhausted to the outside through the air exhaust flow path 326.

In the embodiment, an auxiliary air flow path is defined by the inner housing member 222 and a sleeve member 336 attached to the inner housing member. Referring to FIGS. 8 and 11 to 13, the inner housing member 222 has a first annular wall 340 disposed in its other end portion, and a second annular wall 342 in the middle portion in succession to the first annular wall 340. A connecting wall 344 which connects the first and second annular walls 340 and 324 together and which extends in a radial direction is disposed between the walls. The first turbine blade portion 332 of the rotor 274 is placed on an inside of the first annular wall 340, the second turbine blade portion 334 of the rotor 274 is placed on an inside of the second annular wall 342, and the end surfaces of the second blade portions 281 of the first turbine blade portion 332 are placed on an inside of the connecting wall 344.

Flow path openings 346 are formed in the connecting wall 344 and the second annular wall 342 of the inner housing member 222. Plural flow path openings 346 are disposed in the circumferential direction of the inner housing member 222 at intervals. The sleeve member 336 is attached to the outer peripheral surface of the inner housing member 222 so as to cover the whole of the flow path openings 346. In the embodiment, a male thread 348 is formed in the outer peripheral surface of the second annular wall 342. A female thread of the sleeve member 336 is screwed with the male thread 348. The sleeve member 336 arcuately extends from the male thread 348 to the end surface of the first annular wall 340 in an outward radial direction of the inner housing member 222, so as to cover the flow path openings 346. According to this configuration, the inner housing member 222 and the sleeve member 336 form an auxiliary air flow path which guides air from the first turbine blade portion 332 to the second turbine blade portion 334. One end portion of each flow path opening 346, i.e., the portion opened to the connecting wall 344 functions as an introduction opening through which the air from the first turbine blade portion 332 is introduced. The other end portion of each flow path opening 346, i.e., the portion opened to the second annular wall 342 functions as a second nozzle opening from which the air flowing through the auxiliary air flow path is injected toward the second turbine blade portion The inner housing member 222 and the sleeve member 336 are preferably formed by metal injection molding, powder sintering, or synthetic resin molding. When the members are formed by such a method, the members can be produced relatively easily and economically. It is a matter of course that the members 222 and 336 may be formed also by a cutting work. In the case where the members are formed by synthetic resin molding, polyphenylene sulfide (PPS), fluororesin, polyether imide, polyether ether ketone, liquid crystal polymer, aromatic polyolefin, polycarbonate, phenol resin, or the like is preferably used as the resin material. When the members are made of such a synthetic resin material, the members can have sufficient rigidity and heat resistance. Alternatively, only one of the inner housing member and the sleeve member 336 may be formed as described above.

Figure 11:
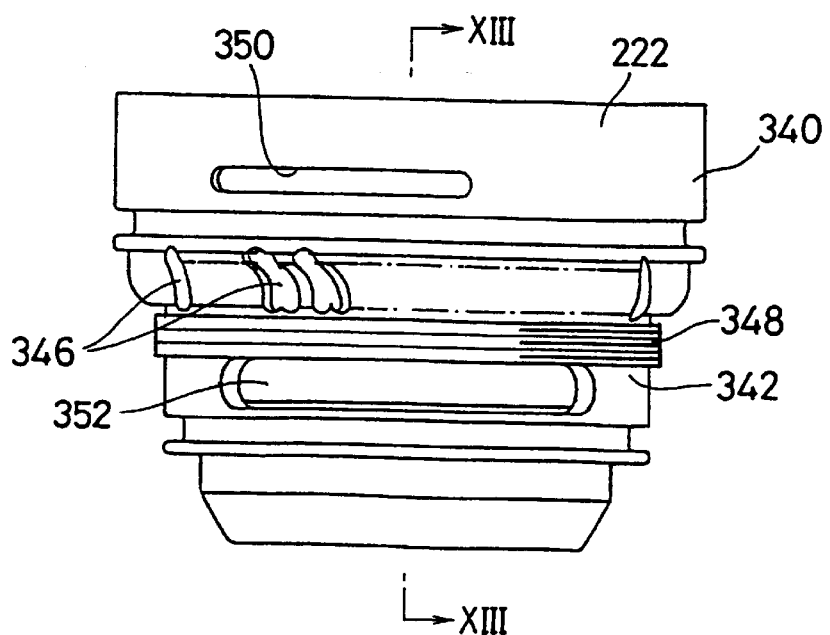
FIG. 11 is a front view showing an inner housing member of the handpiece of FIG. 8.
Figure 12:
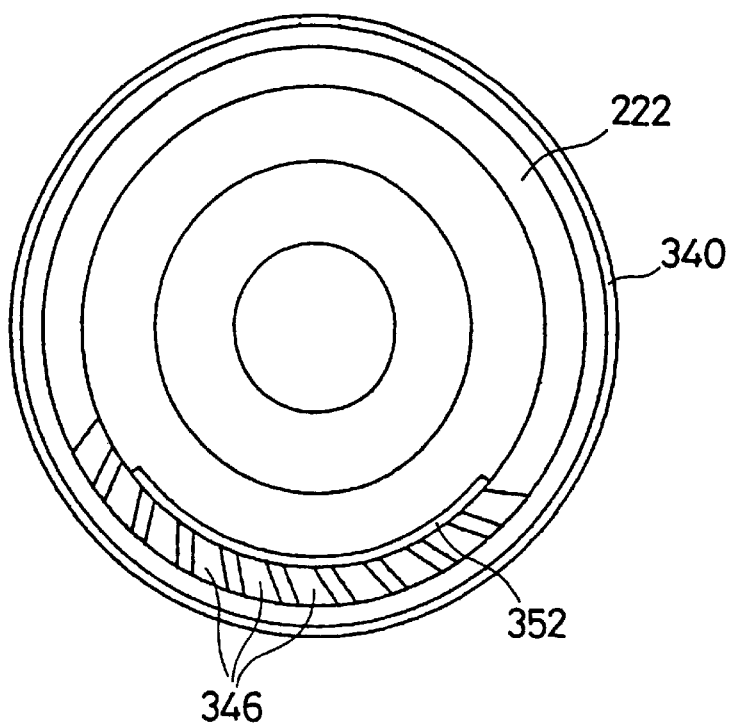
FIG. 12 is a plan view showing the inner housing member of FIG. 11.
Figure 13:
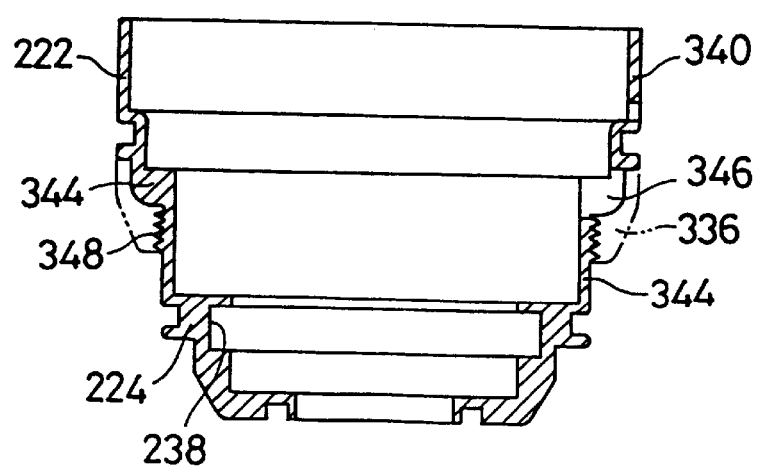
FIG. 13 is a section view taken along a line XIII—XIII of FIG. 11.

In the second embodiment, as shown in FIGS. 11 and 12, an opening 350 which corresponds to the nozzle opening 290 is formed at one end of the inner housing member 222. The opening 350 is slightly larger than the nozzle opening 290. Therefore, the air injected from the nozzle opening 290 is supplied into the first turbine blade portion 332 through the opening 350. An opening 352 which corresponds to the exhaust opening 320 is formed at a middle portion of the inner housing member 222. The opening 352 is slightly larger than the exhaust opening 320. Therefore, the air from the second turbine blade portion 334 is supplied to the exhaust opening 320 through the opening 352. Also in the second embodiment, a water supply flow path for injecting water, an air supply flow path for injecting air, and a configuration associated with the flow paths are omitted.

Referring mainly to FIGS. 8 and 9, an operation of the handpiece of the second embodiment will be described. The driving air from the air supply source (not shown) is supplied to the air flow path 292 of the flow path member 216 through the air supply tube (not illustrated) incorporated in the grip body 206 and the air feed tube 304, and then injected from the nozzle opening 290 toward the first turbine blade portions 278 of the first turbine blade portion 332 of the rotor 274. At this time, since the nozzle opening 290 is opened in a direction which is substantially perpendicular to the rotation axis 210, the air from the nozzle opening 290 is injected in a radial direction which is substantially perpendicular to the rotation axis 210 and then acts on the first turbine blade portion 332. Therefore, the injected air efficiently acts on the first turbine blade portion 332, whereby the rotation torque of the rotor 274 can be increased. The air injected from the nozzle opening 290 is guided by the partition walls 312 and 314. Although the nozzle opening 290 has the large arc width in the circumferential direction, therefore, the air is prevented from being biased in the width direction of the nozzle opening, and injected substantially uniformly in the width direction.

The air injected from the nozzle opening 290 first acts on the operating surfaces of the turbine blade portions 278 of the first turbine blade portion 332. Specifically, the air acts on the operating surfaces 280a of the first blade portions 280 of the first turbine blade portion 278, flows along the operating surfaces 280a in the direction opposite to the rotation direction indicated by the arrow 284 (FIG. 9), and further flows downward along the operating surfaces 281a of the second blade portions 281 in a direction separating from the first blade portions 280 and in the direction opposite to the rotation direction. In this way, in the first turbine blade portion 332, the air injected from the nozzle opening 290 flows smoothly downward in the direction opposite to the rotation direction as indicated by the solid lines with arrows in FIG. 15. Consequently, the rotor 274 can be efficiently rotated. Since air flows smoothly, the flow velocity of the air is less reduced and a loss of the kinetic energy of the air is made small, so that high rotation torque can be obtained.

The air which flows along the first turbine blade portion 278 of the first turbine blade portion 332 is guided to one end of each of the flow path openings 346 and then injected from the other ends of the openings toward the second turbine blade portions 279 of the second turbine blade portion 334 of the rotor 274 through the flow path openings 346. The other ends of the flow path openings 346 functioning as the second nozzle openings are opened to the second annular wall 342 which is substantially parallel with the rotation axis 210. In other words, the other ends are opened in a direction which is substantially perpendicular to the rotation axis 210. Therefore, the air from the other ends of the flow path openings 346 acts on the second turbine blade portion 334 in a direction which is substantially perpendicular to the rotation axis 210 so as to efficiently act on the blade portion 334. Furthermore, the flow path openings 346 are disposed in a relatively wide range in the circumferential direction, for example, at an angle range of 90 to 120 deg., and hence the air acts on the plurality of second turbine blade portions 279 of the second turbine blade portion 334, thereby suppressing the torque ripple of the second turbine blade portion 334.

Figure 15:
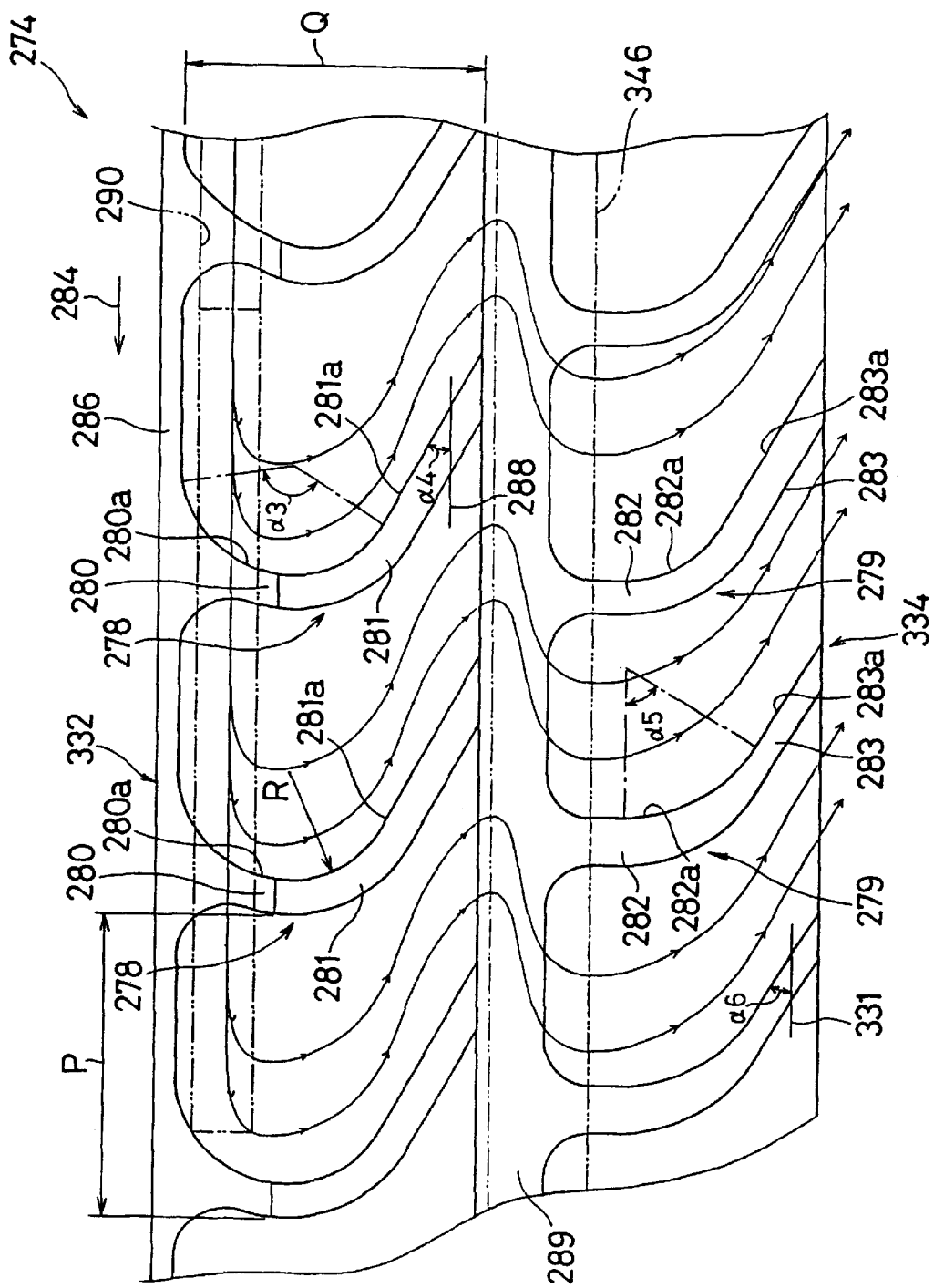
FIG. 15 is a development view showing the rotor of FIG. 14.

As shown in FIG. 15, the air injected from the other ends of the flow path openings 346 is injected toward the upper end portions of the first blade portions 282 of the second turbine blade portions 279 of the second turbine blade portion 334 and acts on the operating surfaces 282a of the first blade portions 282. The air which acts on the operating surfaces 282a of the first blade portions 282 of the second turbine blade portions 279 flows along the operating surfaces 282a in the direction opposite to the rotation direction indicated by the arrow 284 (FIG. 9), and further flows along the operating surfaces 283a of the second blade portions 283 in a direction separating from the first blade portions 282 and in the direction opposite to the rotation direction. In this way, also in the second turbine blade portion 334, the air injected from the flow path openings 346 flows smoothly downward in the direction opposite to the rotation direction as indicated by the solid lines with arrows in FIG. 15. Consequently, the injected air is prevented from becoming a rotation resistance to the second turbine blade portion 334, with the result that high rotation torque can be obtained.

In the second embodiment, the air which has acted on the first turbine blade portion 332 successively acts on the second turbine blade portion 334. Therefore, the embodiment has the following features. The air injected toward the first turbine blade portion 332 is relatively high in pressure and velocity, and hence the air functions so as to rotate the rotor 274 at a high velocity. By contrast, the air injected toward the second turbine blade portion 334 is slightly lowered in pressure and velocity because the air has acted on the first turbine blade portion 332. Consequently, the air acts on the second turbine blade portion 334 so as to slightly lower the rotational velocity of the rotor instead of raising the velocity, and to increase the rotation torque. As a result, the supply of air from the nozzle opening 290 through the first turbine blade portion 332 and the second turbine blade portion 334 can increase the rotation torque of the rotor 274 while suppressing the rise of the rotational velocity of the rotor. As easily understood from the above description, the number of rotations and the rotation torque of the rotor 274 can be adjusted by somewhat changing the flow direction of the air injected to the second turbine blade portion 334.

The air which has acted on the second turbine blade portion 334 is guided to the exhaust opening 320 along the second turbine blade portions 279 and then exhausted to the outside from the exhaust opening 320 through the exhaust flow path 322 and the air exhaust flow path 326.

The above-described second embodiment is configured so that the air injected from the nozzle opening 290 is guided downward in the direction opposite to the rotation direction along the operating surface of the first turbine blade portion 332 of the rotor 274, and further guided downward in the direction opposite to the rotation direction along the operating surface of the second turbine blade portion 334. By contrast, the air injected from the nozzle opening 290 may be guided upward in the direction opposite to the rotation direction. In this case, the second turbine blade portion 334 is disposed above the first turbine blade portion 332 of the rotor 274, and, in accordance with this disposition, the exhaust opening 320 is placed above the nozzle opening 290.

In the second embodiment, since the first and second turbine blade portion s 332 and 334 are connected to each other via the intermediate wall 289, the rotor 274 itself can be miniaturized. This configuration can reduce the size of the head portion 204 of the handpiece and particularly the height of the head portion. Therefore, the handpiece can be advantageously used in a cutting operation of molars or dental treatment for children.

The invention may be embodied in other specific forms without departing from the sprit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An air turbine handpiece comprising:
   a grip portion,
   a head portion disposed at a tip of the grip portion, and
   a rotor having a turbine blade portion, disposed in a chamber formed in the head portion, the rotor being rotatably supported via bearing means, integrally with a rotation shaft, a tool being detachably attached to the rotation shaft,
   wherein a nozzle opening for injecting air toward the turbine blade portion of the rotor, and an exhaust opening for exhausting the injected air to an outside are opened to the chamber of the head portion, and an arc width W of the nozzle opening in a circumferential direction is set to two or more times a height H of the rotor in a rotation axial direction.

2. The air turbine handpiece of claim 1, wherein the arc width W of the nozzle opening in the circumferential direction is three to twenty times the height H in the rotation axial direction of the rotor (3 H≦W≦20 H).

3. The air turbine handpiece of claim 2, wherein the arc width W of the nozzle opening in the circumferential direction is seven to fifteen times the height H in the rotation axial direction of the rotor (7 H≦W≦15 H).

4. The air turbine handpiece of claim 1, wherein a plurality of turbine blades are arranged in the turbine blade portion in the circumferential direction at substantially regular intervals, and the arc width W in the circumferential direction of the nozzle opening is larger than two times a pitch width P of the plurality of turbine blades.

5. An air turbine handpiece comprising:

a grip portion, a head portion disposed at a tip end of the grip portion, and a rotor having a turbine blade portion, disposed in a chamber formed in the head portion, the rotor being rotatably supported via bearing means, integrally with a rotation shaft, a tool being detachably attached to the rotation shaft, wherein the turbine blade portion of the rotor has a hub and a plurality of turbine blades which are arranged on an outer peripheral surface of the hub in a circumferential direction at substantially regular intervals, each of the turbine blades has a first blade portion which extends in a substantially projected arcuate form in a rotation direction of the rotor, and a second blade portion which is substantially continuous with the first blade portion and which extends in a direction separating from the first blade portion and in a direction opposite to the rotation of the rotor, a nozzle opening for injecting air toward the first blade portions of the turbine blades, and an exhaust opening for exhausting the air which has been injected toward the turbine blades, to an outside are opened to the chamber, and air which has been injected from the nozzle opening to the first blade portions of the turbine blades is guided by the first blade portions to flow in the direction opposite to the rotation direction, then guided by the second portions in the direction separating from the first blade portions and in the direction opposite to the rotation direction, and thereafter exhausted to the outside through the exhaust opening.

6. The air turbine handpiece of claim 5, wherein the hub of the turbine blade has a first portion having an outer peripheral surface which extends in a substantially recessed arcuate form in an inward radial direction of the rotor, and a second portion which extends from the first portion in a rotation axial direction of the rotor, and a part of the air injected from the nozzle opening is guided by the first and second portions of the hub and then directed toward the turbine blades.

7. The air turbine handpiece of claim 5, wherein the first blade portions of the plurality of turbine blades are formed in the shape of circular arc having a radius of curvature which is 1.5 or more times the height H of the nozzle opening in the rotation axial direction.

8. The air turbine handpiece of claim 5, wherein the second blade portions of the plurality of turbine blades extend in the direction opposite to the rotation direction, inclined at an angle of 15 to 45 deg. with respect to a plane which is substantially perpendicular to the rotation axis of the rotor.

9. The air turbine handpiece of claim 5, wherein the hub and the plurality of turbine blades of the turbine blade portion are integrally formed by synthetic resin molding, powder sintering, or metal injection molding.

10. The air turbine handpiece of claim 9, wherein a synthetic resin material used in the synthetic resin molding is one of polyphenylene sulfide (PPS), fluororesin, polyether imide, polyether ether ketone, liquid crystal polymer, aromatic polyolefin, polycarbonate, and phenol resin.

11. The air turbine handpiece of claim 5, wherein the hub and the plurality of turbine blades of the turbine blade portion are integrally formed by synthetic resin molding, a cylindrical insert part is inserted into the hub, and projections and depressions for enhancing coupling between the hub and the insert part are formed on an outer peripheral surface of the insert part.

12. The air turbine handpiece of claim 5, wherein an arc width W in a circumferential direction of the nozzle opening which is opened to the chamber is larger than two times the height H in a rotation axial direction of the rotor.

13. The air turbine handpiece of claim 12, wherein an air flow path which guides air to the nozzle opening is disposed in the head portion, and a partition wall which guides air to the nozzle opening is disposed in the air flow path.

14. The air turbine handpiece of claim 13, wherein the head portion comprises a head body and a flow path member which cooperate with each other to form the chamber, the air flow path is formed between the head body and the flow path member by attaching the flow path member to the head body, and the partition wall is disposed on the flow path member.

15. The air turbine handpiece of claim 14, wherein a fitting hole which communicates with the air flow path is formed in one end portion of the flow path member, and one end of an air feed tube for feeding air is connected to the fitting hole.

16. The air turbine handpiece of claim 14, wherein the flow path member is formed by plastic working, synthetic resin molding, or powder sintering.

17. An air turbine handpiece comprising:

a grip portion, a head portion disposed at a tip of the grip portion, and a rotor disposed in a chamber formed in the head portion, the rotor being rotatably supported via bearing means, integrally with a rotation shaft, a tool being detachably attached to the rotation shaft, wherein the rotor has first and second turbine blade portions, a nozzle opening for injecting air toward the first turbine blade portion, and an exhaust opening for exhausting the injected air to an outside are opened to the chamber, air injected from the nozzle opening acts on the first turbine blade portion in a direction which is substantially perpendicular to the rotation axis of the rotor, is then guided from the first turbine blade portion to the second turbine blade portion, acts on the second turbine blade portion in a direction which is substantially perpendicular to the rotation axis of the rotor, and is thereafter exhausted from the second turbine blade portion to the outside through the exhaust opening.

18. The air turbine handpiece of claim 17, wherein the first turbine blade portion of the rotor has a first hub and a plurality of first turbine blades which are arranged on an outer peripheral surface of the first hub in a circumferential direction at intervals, each of the first turbine blades has a first blade portion which extends in a substantially projected arcuate form in a rotation direction of the rotor, and a second blade portion which is substantially continuous with the first blade portion and which extends in a direction separating from the first blade portion and in a direction opposite to the rotation direction of the rotor, the second turbine blade portion has a second hub and a plurality of second turbine blades which are arranged on an outer peripheral surface of the second hub in the circumferential direction at intervals, each of the second turbine blades has a first blade portion which extends in a substantially projected arcuate form in the rotation direction of the rotor and a second blade portion which is substantially continuous with the first blade portion and which extends in a direction separating from the first blade portion and in a direction opposite to the rotation direction of the rotor, and air injected from the nozzle opening acts on the first blade portions of the first turbine blades of the first turbine blade portion, then the air is guided by the first blade portions to flow in the direction opposite to the rotation direction, further guided by the second blade portions of the first turbine blades in a direction separating from the first blade portions and in the direction opposite to the rotation direction, and the air thereafter acts on the first blade portions of the second turbine blades of the second turbine blade portion, is guided by the first blade portions in the direction opposite to the rotation direction, further guided by the second blade portions of the second turbine blades in the direction opposite to the rotation direction, and thereafter exhausted to the outside through the exhaust opening.

19. The air turbine handpiece of claim 18, wherein the first hub of the first turbine blade portion has a first portion having an outer peripheral surface which extends in a substantially recessed arcuate form in an inward radial direction of the rotor, and a second portion which extends from the first portion in a rotation axial direction of the rotor, and a part of the air injected from the nozzle opening is guided by the first and second portions of the first hub and then directed toward the first turbine blades of the first turbine blade portion.

20. The air turbine handpiece of claim 19, wherein the first blade portions of the first turbine blades of the first turbine blade portion of the rotor are formed into the shape of a circular arc having a radius of curvature which is 1.5 or more times the height H of the nozzle opening in the rotation axial direction.

21. The air turbine handpiece of claim 18, wherein the second hub of the second turbine blade portion has a first portion having an outer peripheral surface which extends in a substantially recessed arcuate form in an inward radial direction of the rotor, and a second portion which extends from the first portion in a rotation axial direction of the rotor, and a part of the air injected toward the second turbine blade portion is guided by the first and second portions of the second hub and then directed toward the second turbine blade portions of the second turbine blade portion.

22. The air turbine handpiece of claim 18, wherein the second blade portions of the first and second turbine blades extend in the direction opposite to the rotation direction, inclined at an angle of 15 to 45 deg. with respect to a plane which is substantially perpendicular to the rotation axis of the rotor.

23. The air turbine handpiece of claim 18, wherein the arc width W of the nozzle opening in the circumferential direction is three to twenty times the height H in the rotation axial direction of the rotor ($3H \leq W \leq 20H$).

24. The air turbine handpiece of claim 23, wherein the arc width W of the nozzle opening in the circumferential direction is seven to fifteen times the height H in the rotation axial direction of the rotor ($7H \leq W \leq 15H$).

25. The air turbine handpiece of claim 17, wherein the head portion comprises a head body which forms the chamber, an inner housing member is attached to an interior of the chamber of the head body, a sleeve member is attached to an outer peripheral surface of the inner housing member, and an auxiliary air flow path which guides air from the first turbine blade portion to the second turbine blade portion is formed by the sleeve member and the inner housing member.

26. The air turbine handpiece of claim 25, wherein a plurality of flow path openings are disposed in the inner housing member in a circumferential direction at intervals, and the sleeve member is attached to the inner housing member so as to cover the plurality of flow path openings, thereby the flow path openings function as the auxiliary air flow path, and air from the first turbine blade portion is introduced from one end of each of the flow path openings and then injected toward the second turbine blade portion from other ends of the flow path openings.

27. The air turbine handpiece of claim 25, wherein the inner housing member and/or the sleeve member are formed by metal injection molding, powder sintering, or synthetic resin molding.

28. The air turbine handpiece of claim 27, wherein a synthetic resin material used in the synthetic resin molding is one of polyphenylene sulfide (PPS), fluororesin, polyether imide, polyether ether ketone, liquid crystal polymer, aromatic polyolefin, polycarbonate, and phenol resin.

29. The air turbine handpiece of claim 17, wherein the first and second turbine blade portions of the rotor are integrally formed by synthetic resin molding, powder sintering, or metal injection molding.

30. The air turrbine handpiece of claim 17, wherein the first and second turbine blade portions of the rotor are integrally formed by synthetic resin molding, a cylindrical insert part is inserted across the first and second turbine blade portions, the cylindrical part having an outer peripheral surface onn which projections and depressions for enhancing coupling of the portions are formed.

31. The air turbine handpiece of claim 17, wherein an arc width W in a circumferential direction of the nozzle opening which is opened to the chamber is larger than two times the height H in a rotation axial direction of the rotor.

32. The air turbine handpiece of claim 31, wherein a plurality of turbine blades are arranged in the turbine blade portion in the circumferential direction at substantially regular intervals, and the arc width W in the circumferential direction of the nozzle opening is larger than two times a pitch width P of the plurality of turbine blades.

33. The air turbine handpiece of claim 31, wherein an air flow path which guides air to the nozzle opening is disposed in the head portion, and a partition wall which guides air to the nozzle opening is disposed in the air flow path.

* * * * *